United States Patent
Mandrusov et al.

(10) Patent No.: US 8,608,661 B1
(45) Date of Patent: *Dec. 17, 2013

(54) METHOD FOR INTRAVASCULAR DELIVERY OF A TREATMENT AGENT BEYOND A BLOOD VESSEL WALL

(75) Inventors: Evgenia Mandrusov, Campbell, CA (US); Eugene T. Michal, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1350 days.

This patent is subject to a terminal disclaimer.

(21) Appl. No.: 10/792,960

(22) Filed: Mar. 3, 2004

Related U.S. Application Data

(63) Continuation-in-part of application No. 10/011,071, filed on Nov. 30, 2001, now Pat. No. 6,702,744.

(51) Int. Cl.
    *A61B 8/00* (2006.01)
(52) U.S. Cl.
    USPC ......... 600/439; 600/437; 600/466; 600/467; 424/484; 424/93.1; 424/93.73
(58) Field of Classification Search
    USPC ................ 600/437, 439, 466, 467; 424/484, 424/93.1–93.73
    See application file for complete search history.

(56) References Cited

U.S. PATENT DOCUMENTS

| | | |
|---|---|---|
| 2,512,569 A | 6/1950 | Saffir |
| 3,584,624 A | 6/1971 | de Ciutiis |
| 3,780,733 A | 12/1973 | Martinez-Manzor |
| 3,890,976 A | 6/1975 | Bazell et al. |
| 4,141,973 A | 2/1979 | Balazs |
| 4,617,186 A | 10/1986 | Schafer et al. |
| 4,794,931 A | 1/1989 | Yock |
| 4,818,291 A | 4/1989 | Iwatsuki et al. |
| 4,842,590 A | 6/1989 | Tanabe et al. |
| 5,000,185 A | 3/1991 | Yock |
| 5,024,234 A | 6/1991 | Leary et al. |
| 5,049,130 A | 9/1991 | Powell |

(Continued)

FOREIGN PATENT DOCUMENTS

| | | |
|---|---|---|
| EP | 0331584 | 9/1989 |
| EP | 0861632 | 9/1998 |

(Continued)

OTHER PUBLICATIONS

Abbott Cardiovascular Systems Inc, PCT International Preliminary Report on Patentability and Written Opinion mailed Dec. 24, 2008 for PCT Application No. PCT/US2007/013181, 11 pages.

(Continued)

*Primary Examiner* — James Kish
(74) *Attorney, Agent, or Firm* — Randy Shen; Blakely Sokoloff Taylor & Zafman LLP

(57) ABSTRACT

A method including positioning a delivery device at a location in a blood vessel; advancing the delivery device a distance into a wall of the blood vessel to a treatment site beyond an external elastic lamina of the blood vessel; and after advancing the delivery device, introducing a treatment agent including a cellular component through the delivery device. A composition including a treatment agent comprising a cellular component associated with a matrix material, wherein the composition is suitable for percutaneous delivery. Also an apparatus suitable for delivering a treatment agent. Also, a kit including a treatment agent.

20 Claims, 9 Drawing Sheets

(56) References Cited

U.S. PATENT DOCUMENTS

| | | | |
|---|---|---|---|
| 5,092,848 A | 3/1992 | DECiutiis | |
| 5,100,185 A | 3/1992 | Menke et al. | |
| 5,109,859 A | 5/1992 | Jenkins | |
| 5,116,317 A * | 5/1992 | Carson et al. | 604/102.01 |
| 5,128,326 A | 7/1992 | Balazs et al. | |
| 5,171,217 A | 12/1992 | March et al. | |
| 5,202,745 A | 4/1993 | Sorin et al. | |
| 5,203,338 A | 4/1993 | Jang | |
| 5,270,300 A | 12/1993 | Hunziker | |
| 5,291,267 A | 3/1994 | Sorin et al. | |
| 5,306,250 A | 4/1994 | March et al. | |
| 5,321,501 A | 6/1994 | Swanson et al. | |
| 5,328,955 A | 7/1994 | Rhee et al. | |
| 5,336,252 A | 8/1994 | Cohen | |
| 5,354,279 A * | 10/1994 | Hofling | 604/164.12 |
| 5,365,325 A | 11/1994 | Kumasaka et al. | |
| 5,372,138 A | 12/1994 | Crowley et al. | |
| 5,380,292 A | 1/1995 | Wilson | |
| 5,437,632 A | 8/1995 | Engelson | |
| 5,455,039 A | 10/1995 | Edelman et al. | |
| 5,459,570 A | 10/1995 | Swanson et al. | |
| 5,464,395 A | 11/1995 | Faxon et al. | |
| 5,465,147 A | 11/1995 | Swanson | |
| 5,485,486 A | 1/1996 | Gilhousen et al. | |
| 5,499,630 A | 3/1996 | Hiki et al. | |
| 5,516,532 A * | 5/1996 | Atala et al. | 424/548 |
| 5,540,912 A | 7/1996 | Roorda et al. | |
| 5,546,948 A | 8/1996 | Hamm et al. | |
| 5,554,389 A | 9/1996 | Badylak et al. | |
| 5,575,815 A | 11/1996 | Slepian et al. | |
| 5,580,714 A | 12/1996 | Polovina | |
| 5,580,856 A | 12/1996 | Prestrelski et al. | |
| 5,588,432 A | 12/1996 | Crowley | |
| 5,621,610 A | 4/1997 | Moore et al. | |
| 5,642,234 A | 6/1997 | Altman et al. | |
| 5,655,548 A | 8/1997 | Nelson et al. | |
| 5,667,778 A | 9/1997 | Atala | |
| 5,672,153 A | 9/1997 | Lax et al. | |
| 5,676,151 A | 10/1997 | Yock | |
| 5,693,029 A | 12/1997 | Leonhardt | |
| 5,722,403 A | 3/1998 | McGee et al. | |
| 5,725,551 A | 3/1998 | Myers et al. | |
| 5,730,732 A | 3/1998 | Sardelis et al. | |
| 5,740,808 A | 4/1998 | Panescu et al. | |
| 5,749,915 A | 5/1998 | Slepian | |
| 5,785,689 A | 7/1998 | De Toledo et al. | |
| 5,810,885 A | 9/1998 | Zinger | |
| 5,811,533 A | 9/1998 | Gold et al. | |
| 5,827,313 A | 10/1998 | Ream et al. | |
| 5,843,156 A | 12/1998 | Slepian et al. | |
| 5,874,500 A | 2/1999 | Rhee et al. | |
| 5,879,713 A | 3/1999 | Roth et al. | |
| 5,900,433 A | 5/1999 | Igo et al. | |
| 5,906,934 A | 5/1999 | Grande et al. | |
| 5,919,449 A | 7/1999 | Dinsmore | |
| 5,935,160 A | 8/1999 | Auricchio et al. | |
| 5,939,323 A | 8/1999 | Valentini et al. | |
| 5,941,868 A | 8/1999 | Kaplan et al. | |
| 5,957,941 A | 9/1999 | Ream | |
| 5,968,064 A | 10/1999 | Selmon | |
| 5,979,449 A | 11/1999 | Steer | |
| 5,980,887 A | 11/1999 | Isner et al. | |
| 5,981,568 A | 11/1999 | Kunz et al. | |
| 5,984,908 A | 11/1999 | Davis et al. | |
| 5,997,536 A | 12/1999 | Osswald et al. | |
| 6,022,540 A | 2/2000 | Bruder et al. | |
| 6,045,565 A | 4/2000 | Ellis et al. | |
| 6,050,949 A * | 4/2000 | White et al. | 600/466 |
| 6,051,071 A | 4/2000 | Charvet et al. | |
| 6,051,648 A | 4/2000 | Rhee et al. | |
| 6,056,744 A | 5/2000 | Edwards | |
| 6,058,329 A | 5/2000 | Salo et al. | |
| 6,060,053 A | 5/2000 | Atala | |
| 6,071,305 A | 6/2000 | Brown et al. | |
| 6,086,582 A | 7/2000 | Altman et al. | |
| 6,093,177 A | 7/2000 | Javier, Jr. et al. | |
| 6,099,563 A | 8/2000 | Zhong | |
| 6,099,864 A | 8/2000 | Morrison et al. | |
| 6,102,887 A | 8/2000 | Altman | |
| 6,102,904 A | 8/2000 | Vigil et al. | |
| 6,102,926 A | 8/2000 | Tartaglia et al. | |
| 6,120,520 A | 9/2000 | Saadat et al. | |
| 6,120,904 A | 9/2000 | Hostettler et al. | |
| 6,127,448 A | 10/2000 | Domb | |
| 6,133,231 A | 10/2000 | Ferrara et al. | |
| 6,134,003 A | 10/2000 | Tearney et al. | |
| 6,151,525 A | 11/2000 | Soykan | |
| 6,152,141 A | 11/2000 | Stevens et al. | |
| 6,153,428 A | 11/2000 | Gustafsson et al. | |
| 6,159,443 A | 12/2000 | Hallahan et al. | |
| 6,162,202 A | 12/2000 | Sicurelli et al. | |
| 6,175,669 B1 | 1/2001 | Colston et al. | |
| 6,177,407 B1 | 1/2001 | Rodgers et al. | |
| 6,179,809 B1 | 1/2001 | Khairkhahan et al. | |
| 6,183,432 B1 | 2/2001 | Milo | |
| 6,183,444 B1 | 2/2001 | Glines et al. | |
| 6,187,330 B1 | 2/2001 | Wang et al. | |
| 6,190,353 B1 | 2/2001 | Makower et al. | |
| 6,191,144 B1 | 2/2001 | Isner | |
| 6,192,271 B1 | 2/2001 | Hayman | |
| 6,193,763 B1 | 2/2001 | Mackin | |
| 6,197,324 B1 | 3/2001 | Crittenden | |
| 6,201,608 B1 | 3/2001 | Mandella et al. | |
| 6,206,893 B1 | 3/2001 | Klein et al. | |
| 6,206,914 B1 | 3/2001 | Soykan et al. | |
| 6,207,180 B1 | 3/2001 | Ottoboni et al. | |
| 6,210,392 B1 | 4/2001 | Vigil et al. | |
| 6,217,527 B1 | 4/2001 | Selmon et al. | |
| 6,217,554 B1 | 4/2001 | Green | |
| 6,221,049 B1 | 4/2001 | Selmon et al. | |
| 6,231,546 B1 | 5/2001 | Milo et al. | |
| 6,235,000 B1 | 5/2001 | Milo et al. | |
| 6,241,710 B1 | 6/2001 | Van Tassel et al. | |
| 6,251,104 B1 | 6/2001 | Kesten et al. | |
| 6,283,947 B1 | 9/2001 | Mirzaee | |
| 6,287,285 B1 | 9/2001 | Michal et al. | |
| 6,290,729 B1 | 9/2001 | Slepian et al. | |
| 6,296,602 B1 | 10/2001 | Headley | |
| 6,299,604 B1 | 10/2001 | Ragheb et al. | |
| 6,309,370 B1 | 10/2001 | Haim et al. | |
| 6,312,725 B1 | 11/2001 | Wallace et al. | |
| 6,315,994 B2 | 11/2001 | Usala et al. | |
| 6,323,278 B2 | 11/2001 | Rhee et al. | |
| RE37,463 E | 12/2001 | Altman | |
| 6,328,229 B1 | 12/2001 | Duronio et al. | |
| 6,331,309 B1 | 12/2001 | Jennings, Jr. et al. | |
| 6,333,194 B1 | 12/2001 | Levy et al. | |
| 6,334,872 B1 | 1/2002 | Termin et al. | |
| 6,338,717 B1 | 1/2002 | Ouchi | |
| 6,346,098 B1 | 2/2002 | Yock et al. | |
| 6,346,099 B1 | 2/2002 | Altman | |
| 6,346,515 B1 | 2/2002 | Pitaru et al. | |
| 6,358,247 B1 | 3/2002 | Altman et al. | |
| 6,358,258 B1 | 3/2002 | Arcia et al. | |
| 6,360,129 B1 | 3/2002 | Ley et al. | |
| 6,368,285 B1 | 4/2002 | Osadchy et al. | |
| 6,371,935 B1 | 4/2002 | Macoviak et al. | |
| 6,371,992 B1 | 4/2002 | Tanagho et al. | |
| 6,379,379 B1 | 4/2002 | Wang | |
| 6,385,476 B1 | 5/2002 | Osadchy et al. | |
| 6,391,052 B2 | 5/2002 | Buirge et al. | |
| 6,395,023 B1 | 5/2002 | Summers | |
| 6,409,716 B1 | 6/2002 | Sahatjian et al. | |
| 6,416,510 B1 | 7/2002 | Altman et al. | |
| 6,432,119 B1 | 8/2002 | Saadat | |
| 6,436,135 B1 | 8/2002 | Goldfarb | |
| 6,440,947 B1 | 8/2002 | Barron et al. | |
| 6,443,941 B1 | 9/2002 | Slepian et al. | |
| 6,443,949 B2 | 9/2002 | Altman | |
| 6,447,504 B1 | 9/2002 | Ben-Haim et al. | |
| 6,458,095 B1 | 10/2002 | Wirt et al. | |
| 6,458,098 B1 | 10/2002 | Kanesaka | |
| 6,464,862 B2 | 10/2002 | Bennett et al. | |
| 6,465,001 B1 | 10/2002 | Hubbell et al. | |

(56) References Cited

U.S. PATENT DOCUMENTS

| | | |
|---|---|---|
| 6,478,776 B1 | 11/2002 | Rosenman et al. |
| 6,482,231 B1 | 11/2002 | Abatangelo et al. |
| 6,485,481 B1 | 11/2002 | Pfeiffer |
| 6,494,862 B1 | 12/2002 | Ray et al. |
| 6,514,217 B1 | 2/2003 | Selmon et al. |
| 6,544,230 B1 | 4/2003 | Flaherty et al. |
| 6,548,081 B2 | 4/2003 | Sadozai et al. |
| 6,554,801 B1 * | 4/2003 | Steward et al. .......... 604/164.03 |
| 6,599,267 B1 * | 7/2003 | Ray et al. .................. 604/102.01 |
| 6,602,241 B2 | 8/2003 | Makower et al. |
| 6,616,869 B2 | 9/2003 | Mathiowitz et al. |
| 6,624,245 B2 | 9/2003 | Wallace et al. |
| 6,628,988 B2 | 9/2003 | Kramer et al. |
| 6,629,947 B1 | 10/2003 | Sahatjian et al. |
| 6,632,457 B1 | 10/2003 | Sawhney |
| 6,635,267 B1 | 10/2003 | Miyoshi et al. |
| 6,660,034 B1 | 12/2003 | Mandrusov et al. |
| 6,682,730 B2 | 1/2004 | Mickle et al. |
| 6,689,608 B1 | 2/2004 | Mikos et al. |
| 6,692,466 B1 | 2/2004 | Chow et al. |
| 6,702,744 B2 | 3/2004 | Mandrusov et al. |
| 6,706,034 B1 | 3/2004 | Bhat |
| 6,726,677 B1 | 4/2004 | Flaherty et al. |
| 6,737,072 B1 | 5/2004 | Angele et al. |
| 6,748,258 B1 | 6/2004 | Mueller et al. |
| 6,749,617 B1 | 6/2004 | Palasis et al. |
| 6,759,431 B2 | 7/2004 | Hunter et al. |
| 6,761,887 B1 | 7/2004 | Kavalkovich et al. |
| 6,777,000 B2 | 8/2004 | Ni et al. |
| 6,777,231 B1 | 8/2004 | Katz et al. |
| 6,790,455 B2 | 9/2004 | Chu et al. |
| 6,824,791 B2 | 11/2004 | Mathiowitz et al. |
| 6,858,229 B1 | 2/2005 | Hubbell et al. |
| 6,916,488 B1 | 7/2005 | Meier et al. |
| 6,916,648 B2 | 7/2005 | Goddard et al. |
| 6,926,692 B2 | 8/2005 | Katoh et al. |
| 6,992,172 B1 | 1/2006 | Chang et al. |
| 7,008,411 B1 | 3/2006 | Mandrusov et al. |
| 7,035,092 B2 | 4/2006 | Hillman et al. |
| 7,112,587 B2 | 9/2006 | Timmer et al. |
| 7,129,210 B2 | 10/2006 | Lowinger et al. |
| 7,169,127 B2 | 1/2007 | Epstein et al. |
| 7,273,469 B1 | 9/2007 | Chan et al. |
| 7,361,360 B2 | 4/2008 | Kitabwalla et al. |
| 7,374,774 B2 | 5/2008 | Bowlin et al. |
| 7,438,692 B2 | 10/2008 | Tsonton et al. |
| 7,615,373 B2 | 11/2009 | Simpson et al. |
| 7,732,190 B2 | 6/2010 | Michal et al. |
| 7,815,590 B2 | 10/2010 | Cooper |
| 8,192,760 B2 | 6/2012 | Hossainy et al. |
| 2001/0023349 A1 | 9/2001 | Van Tassel et al. |
| 2001/0055615 A1 * | 12/2001 | Wallace et al. ............... 424/484 |
| 2002/0013408 A1 | 1/2002 | Rhee et al. |
| 2002/0042473 A1 | 4/2002 | Trollsas et al. |
| 2002/0072706 A1 | 6/2002 | Hiblar et al. |
| 2002/0076441 A1 | 6/2002 | Shih et al. |
| 2002/0090725 A1 | 7/2002 | Simpson et al. |
| 2002/0102272 A1 | 8/2002 | Rosenthal et al. |
| 2002/0124855 A1 | 9/2002 | Chachques |
| 2002/0131974 A1 | 9/2002 | Segal |
| 2002/0142458 A1 | 10/2002 | Williams et al. |
| 2002/0146557 A1 | 10/2002 | Claude et al. |
| 2002/0188170 A1 | 12/2002 | Santamore et al. |
| 2003/0023202 A1 | 1/2003 | Nielson |
| 2003/0040712 A1 | 2/2003 | Ray et al. |
| 2003/0050597 A1 | 3/2003 | Dodge et al. |
| 2003/0078671 A1 | 4/2003 | Lesniak et al. |
| 2003/0105493 A1 | 6/2003 | Salo |
| 2003/0175410 A1 | 9/2003 | Campbell et al. |
| 2004/0002650 A1 | 1/2004 | Mandrusov et al. |
| 2004/0181206 A1 | 9/2004 | Chiu et al. |
| 2004/0185084 A1 | 9/2004 | Rhee et al. |
| 2004/0208845 A1 | 10/2004 | Michal et al. |
| 2004/0213756 A1 | 10/2004 | Michal et al. |
| 2004/0229856 A1 | 11/2004 | Chandrasekar et al. |
| 2005/0015048 A1 | 1/2005 | Chiu et al. |
| 2005/0031874 A1 | 2/2005 | Michal et al. |
| 2005/0042254 A1 | 2/2005 | Freyman et al. |
| 2005/0064038 A1 | 3/2005 | Dinh et al. |
| 2005/0065281 A1 | 3/2005 | Lutolf et al. |
| 2005/0070844 A1 | 3/2005 | Chow et al. |
| 2005/0186240 A1 | 8/2005 | Ringeisen et al. |
| 2005/0281883 A1 | 12/2005 | Daniloff et al. |
| 2006/0149392 A1 | 7/2006 | Hsieh et al. |
| 2006/0233850 A1 | 10/2006 | Michal |
| 2007/0270948 A1 | 11/2007 | Wuh |
| 2008/0025943 A1 | 1/2008 | Michal et al. |
| 2012/0225040 A1 | 9/2012 | Hossainy et al. |
| 2012/0225041 A1 | 9/2012 | Hossainy et al. |

FOREIGN PATENT DOCUMENTS

| | | |
|---|---|---|
| EP | 0938871 | 9/1999 |
| EP | 1214077 | 1/2004 |
| GB | 2194144 | 3/1988 |
| JP | 61205446 | 9/1986 |
| JP | 06507106 | 8/1994 |
| JP | 10236984 | 9/1998 |
| JP | 3063935 | 12/1999 |
| JP | 2000502380 | 2/2000 |
| JP | 2000262525 | 9/2000 |
| JP | 2003062089 | 3/2003 |
| WO | WO-92/10142 | 6/1992 |
| WO | WO-9315781 | 8/1993 |
| WO | WO-98/30207 | 7/1998 |
| WO | WO-98/54301 | 12/1998 |
| WO | WO-9953943 | 10/1999 |
| WO | WO-00/16818 | 3/2000 |
| WO | WO-0054661 | 9/2000 |
| WO | WO-00/71196 | 11/2000 |
| WO | WO-01/24775 | 4/2001 |
| WO | WO-0124842 | 4/2001 |
| WO | WO-01/45548 | 6/2001 |
| WO | WO-01/49357 | 7/2001 |
| WO | WO-0200173 | 1/2002 |
| WO | WO-0204008 | 1/2002 |
| WO | WO-02/28450 | 4/2002 |
| WO | WO-02/40070 | 5/2002 |
| WO | WO-02/072166 | 9/2002 |
| WO | WO-02/087623 | 11/2002 |
| WO | WO-03/022909 | 3/2003 |
| WO | WO-03022324 | 3/2003 |
| WO | WO-03/027234 | 4/2003 |
| WO | WO-03026492 | 4/2003 |
| WO | WO-03/064637 | 8/2003 |
| WO | WO 03064637 A1 * | 8/2003 |
| WO | WO-2004/000915 | 12/2003 |
| WO | WO-2004/050013 | 6/2004 |
| WO | WO-2004058305 | 7/2004 |
| WO | WO-2004/066829 | 8/2004 |
| WO | WO-2004/091592 | 10/2004 |
| WO | WO-2004098669 | 11/2004 |
| WO | WO-2005/061019 | 7/2005 |
| WO | WO-2005/067890 | 7/2005 |
| WO | WO-2006/039704 | 4/2006 |
| WO | WO-2006/113407 | 10/2006 |
| WO | WO-2007/048831 | 3/2007 |
| WO | WO-2007145909 | 12/2007 |

OTHER PUBLICATIONS

Abbott Cardiovascular Systems Inc, PCT International Search Report and Written Opinion mailed Feb. 10, 2009 for PCT Application No. PCT/US2007/023419, 17 pages.

Agocha, A., et al., "Hypoxia regulates basal and induced DNA synthesis and collagen type I production in human cardiac fibroblasts: effects of transforming growth factor-beta 1, thyroid hormone, angiotensin II and basic fibroblast growth factor", J. Mol. Cell. Cardiol., 29(8), Apr. 1997, pp. 2233-2244.

Allemann, E., et al., "Kinetics of Blood Component Adsorption on poly(D,L-lactic acid) Nanoparticles: Evidence of Complement C3 Component Involvement", J. Biomed. Mater. Res., 37(2), Abstract downloaded from the Internet at: http://www.ncbi.nlm.nih.gov/

(56) References Cited

OTHER PUBLICATIONS entrez/query.fcgi?cmd=Retrieve&db=PubMed, Nov. 1997, pp. 229-234.
Assmus, B., et al., "Transplantation of Progenitor Cells and Regeneration Enhancement in Acute Myocardial Infarction (Topcare-AMI)", Clinical Investigation and Reports, Oct. 8, 2002, pp. 3009-3017, Department of Molecular Cardiology and Department of hematology (H.M., D.H.) University of Frankfurt, Frankfurt, germany. Circulation Available at http://www.circulationha.org DOI: 10.116.
Baxter, "FloSeal Matrix Hemostatic Sealant", downloaded from the Internet on Nov. 14, 2002, from: http://www.fusionmed.com/docs/surgeon/default.asp, 2 pages.
Berger, et al., "Poly-L-cysteine", J. Am. Chem. Soc., 78(17), Sep. 5, 1956, pp. 4483-4488.
Bernatowicz, M., et al., "Preparation of Boc-[S-(3-nitro-2-pyridinesulfenyl)]-cysteine and its use for Unsymmetrical Disulfide Bond Formation", Int. J. Peptide Protein Res. 28(2), Aug. 1996, pp. 107-112.
Boland, E. D., "Electrospinning Collagen and Elastin: Preliminary Vascular Tissue Engineering", Frontiers in Bioscience, vol. 9, May 1, 2004, pp. 1422-1432.
Brust, G., "Polyimides", downloaded from the Internet at: http://www.pslc.ws/macrog/imide.htm, 2005, 4 pages.
Canderm Pharma, "Technical Dossier: Artecoll", downloaded from the Internet on Oct. 22, 2002 from: http://www.canderm.com/artecoll/tech.html, 3 pages.
Capan, Y., et al., "Preparation and Characterization of Poly(D,L-lactide-co-glycolide) Microspheres for Controlled Release of Human Growth Hormone", AAPS PharmSciTech.; 4(2): article 28, Downloaded from the Internet at: http://www.aapspharmscitech.org/view.asp?art=pt040228&pdf=yes, (2003), 12 pages.
Carpino, L., et al., "Tris(2-aminoethyl)amine as a Substitute for 4-(Aminomethyl)piperidine in the FMOC/Polyamine Approach to Rapid Peptide Synthesis", J. Org. Chem., 55(5), Mar. 1990, pp. 1673-1675.
Chandy, et al., "The development of porous alginate/elastin/PEG composite matrix for cardiovascular engineering", Journal of Biomaterials Applications, vol. 17, Apr. 2003, pp. 287-301.
Choi, Young Seon, et al., "Study on gelatin-containing artificial skin: I. Preparation and characteristics of novel gelatin-alginate sponge", Biomaterials, vol. 20, 1999, 409-417.
Corbett, S., et al., "Covalent Cross-linking of Fibronectin to Fibrin is Required for Maximal Cell Adhesion to a Fibronectin-Fibrin Matrix", The Journal of Biological Chemistry, 272(40), Oct. 3, 1997, pp. 24999-25005.
Creemers, E., et al., "Matrix Metalloproteinase Inhibition After Myocardial Infarction: A New Approach to Prevent Heart Failure?", Circ. Res., vol. 89, 2001, pp. 201-210.
Crivello, et al., "Synthesis and Photoinitiated Cationic Polymerization of Monomers with the Silsesquioxane Core", J Polym Science: Part A: Polymer Chemistry 35, 1997, pp. 407-425.
Davis, M. E., et al., "Injectable Self-Assembling Peptide Nanofibers Create Intramyocardial Microenvironments for Endothelial Cells", Circulation, 111, Feb. 2005, pp. 442-450.
De Rosa, et al., "Biodegradable Microparticles for the Controlled Delivery of Oligonucleotides", International Journal of Pharmaceutics, 242, Aug. 21, 2002, pp. 225-228.
Desai, M., et al., "Polymer bound EDC (P-EDC): A convenient reagent for formation of an amide bond", Tetrahedron Letters, 34(48), Abstract downloaded from the Internet at: http://www.sciencedirect.com, 1 page, Nov. 1993, pp. 7685-7688.
Dinbergs, et al., "Cellular response to transforming growth factor-β1 and basic fibroblast growth factor depends on release kinetics and extracellular matrix interactions", The Journal of Biological Chemistry, vol. 271, No. 47, Nov. 1996, pp. 29822-29829.
Dong, Zhanfeng, et al., "Alginate/gelatin blend films and their properties for drug controlled release", Journal of Membrane Science, vol. 280, 2006, pp. 37-44.
Edelman, "Controlled and modulated release of basic fibroblast growth factor", Biomaterials, vol. 12, Sep. 1999, pp. 619-626.
Etzion, S., et al., "Influence of Embryonic Cardiomyocyte Transplantation on the Progression of Heart Failure in a Rat Model of Extensive Myocardial Infarction", J. Mol. Cell Cardiol., 33, May 2001, pp. 1321-1330.
Ferrara, N., "Role of Vascular Endothelial Growth Factor in the Regulation of Angiogenesis", Kidney International, 56(3), Abstract downloaded from the Internet at: http://www.nature.com/ki/journal/v56/n3/abs/4490967a.html, 1 page, 1999, pp. 794-814.
Friedman, Paul M., et al., "Safety Data of Injectable Nonanimal Stabilized Hyaluronic Acid Gel for Soft Tissue Augmentation," Dermatologic Surgery, 2002, vol. 28, pp. 491-494.
Fuchs, S., et al., "Catheter-Based Autologous Bone Marrow Myocardial Injection in No-Option Patients with Advanced Coronary Artery Disease", J. Am. Coll. Cardiol., 41(10), 2003, pp. 1721-1724.
Fukumoto, S., et al., "Protein Kinase C δ; Inhibits the Proliferation of Vascular Smooth Muscle Cells by Suppressing G1 Cyclin Expression", The Journal of Biological Chemistry, 272(21), May 1997, pp. 13816-13822.
Giordano, F., et al., "Angiogenesis: The Role of the Microenvironment in Flipping the Switch", Current Opinion in Genetics and Development, 11, 2001, pp. 35-40.
Gossler, et al., "Transgenesis by means of blastocyst-derived embryonic stem cell lines", Proc. Natl. Acad. Sci. USA, 83, Dec. 1986, pp. 9065-9069.
Grafe, T. H., "Nanofiber Webs from Electrospinning", Presented at the Nonwovens in Filtration—Fifth International Conference, Stuttgart, Germany, Mar. 2003, pp. 1-5.
Gref, R., et al., "Biodegradable Long-Circulating Polymeric Nanospheres", Science, 263(5153), Abstract downloaded from the Internet at: http://www.sciencemag.org/cgi/content/abstract/263/5153/1600, 1 page, Mar. 1994, pp. 1600-1603.
Grund, F., et al., "Microembolization in Pigs: Effects on Coronary Blood Flow and Myocardial Ischemic Tolerance", Am. J. Physiol., 277 (Heart Circ. Physiol. 46), 1999, pp. H533-H542.
Gupta, et al., "Changes in Passive Mechanical Stiffness of Myocardial Tissue with Aneurysm Formation", Circulation, 89(5), May 1994, pp. 2315-2326.
Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, Jan. 1995, pp. 284-288.
Hashimoto, T., et al., "Development of Alginate Wound Dressings Linked with Hybrid Peptides Derived from Laminin and Elastin", Biomaterials, 25, 2004, pp. 1407-1414.
Haugland, et al., "Dialkylcarbocyanine and Dialkylaminostryryl Probes", Handbook of Fluorescent Probes and Research Products, Molecular Probes, Inc., 2002, pp. 530-534.
Haugland, et al., "Membrane-permeant reactive tracers", Handbook of Fluorescent Probes and Research Products, Molecular Probes, Inc., 2002, pp. 458-553.
Heeschen, C., et al., "Nicotine Stimulates Tumor Angiogenesis", American College of Cardiology, 37(2) Supplement A, Abstract downloaded from the Internet at: http://24.132.160.238/ciw-01acc/abstract_search_author.cfm?SearchName=Heeschen, 1 page, Feb. 2001, pp. 1A-648A.
Hendel, R. C., et al., "Effect of Intracoronary Recombinant Human Vascular Endothelial Growth Factor on Myocardial Perfusion: Evidence for a Dose-Dependent Effect", Circulation, 101, 2000, pp. 118-121.
Henry, R. R., et al., "Insulin Action and Glucose Metabolism in Nondiabetic Control and NIDDM Subjects: Comparison Using Human Skeletal Muscle Cell Cultures", Diabetes, 44(8), Abstract downloaded from the Internet at: http://diabetes.diabetesjournals.org/cgi/content/abstract/44/8/936, 1 page, 1995, pp. 936-946.
Hoffman, "Hydrogels for Biomedical Applications", Advanced Drug Delivery Reviews, vol. 43, 2002, pp. 3-12.
Holland, N. B., et al., "Biomimetic Engineering of Non-Adhesive glycocalyx-like Surfaces Using Oligosaccharide Surfactant Polymers", Nature, 392, Abstract downloaded from the Internet at: http://www.nature.com, 1 page, Apr. 1998, pp. 799-801.

(56) References Cited

OTHER PUBLICATIONS

Horan, R.L., et al., "In Vitro Degradation of Silk Fibroin", Biomaterials, vol. 26, 2004, pp. 3385-3393.
Hovinen, J., et al., "Synthesis of 3'-functionalized oligonucleotides on a single solid support", Tetrahedron Letters, 34(50), Abstract downloaded from the Internet at: http://www.sciencedirect.com, 1 page, Dec. 1993, pp. 8169-8172.
Huang, K., et al., "Synthesis and Characterization of Self-Assembling Block Copolymers Containing Bioadhesive End Groups", Biomacromolecules, 3(2), 2002, pp. 397-406.
Hutcheson, K., et al., "Comparison of Benefits on Myocardial Performance of Cellular Cardiomyoplasty with Skeletal Myoblasts and Fibroblasts", Cell Transplantation, 9(3), 2000, pp. 359-368.
Huynh, T. V., et al., "Constructing and Screening cDNA Libraries in λgt10 and λgt11", Chapter 2 in DNA Cloning, vol. 1: A Practical Approach, ed. By D.M. Glover, 1985, pp. 49-78.
Indik, Z., et al., "Production of Recombinant Human Tropoelastin: Characterization and Demonstration of Immunologic and Chemotactic Activity", Arch. Biochem. Biophys., 280(1), Abstract downloaded from the Internet at: http://www.ncbi.nlm.nih.gov/entrez/query.fcgi?cmd=Retrieve&db=PubMed, 1 page, Jul. 1990, pp. 80-86.
Iskandrian, A. S., et al., "Nuclear Cardiac Imaging: Principles and Applications", second edition, F.A. Davis Co., Philadelphia, cover page, title page and TOC, 1996, 5 pages.
Isner, J. M., "Vascular Endothelial Growth Factor: Gene Therapy and Therapeutic Angiogenesis", Am. J. Cardiol., 82(10A), (Nov. 19, 1998), pp. 63S-64S.
Johnson, et al., "The stabilization and encapsulation of human growth hormone into biodegradable microspheres", Pharmaceutical Research, vol. 14, No. 6, 1997, pp. 730-735.
Jonasson, P., et al., "Denatured states of human carbonic anhydrase II: an NMR study of hydrogen/deuterium exchange at tryptophan-indole-Hn sites", FEBS Letters, 445, 1999, pp. 361-365.
Kaplan, D.L., et al., "Spiderless Spider Webs", Nature Biotechnology, vol. 20, 2002, pp. 239-240.
Kawasuji, M., et al., "Therapeutic Angiogenesis with Intramyocardial Administration of Basic Fibroblast Growth Factor", Ann Thorac Surg, 69, Abstract downloaded from the Internet at: http://ats.ctsnetjournals.org/cgi/content/abstract/69/4/1155, 2 pages, 2000, pp. 1155-1161.
Kelley, et al., "Restraining Infarct Expansion Preserves Left Ventricular Geometry and Function After Acute Anteroapical Infarction", Circulation, 99, 1999, pp. 135-142.
Kelly, E. B., "Advances in Mammalian and Stem Cell Cloning", Genetic Engineering News, vol. 23, No. 7, Apr. 1, 2003, pp. 17-18 & 68.
Khademhosseini, et al., "Microscale Technologies for Tissue Engineering and Biology", PNAS, vol. 103, No. 8, Feb. 21, 2006, pp. 2480-2487.
Kim, D., et al., "Glow Discharge Plasma Deposition (GDPD) Technique for the Local Controlled Delivery of Hirudin from Biomaterials", Pharmaceutical Research, 15(5), 1998, pp. 783-786.
Kim, Ung-Jin, et al., "Structure and Properties of Silk Hydrogels", Biomacromolecules, vol. 5(3), 2004, pp. 786-792.
Kinart, et al., "Electrochemical Studies of 2-hydroxy-3-(3,4-dimethyl-9-oxo-9H-thioxanthen-2-yloxy)N,N,N-trimethyl-1-propanium chloride", J. Electroanal. Chem, 294, 1990, pp. 293-297.
Klein, S., et al., "Fibroblast Growth Factors as Angiogenesis Factors: New Insights Into Their Mechanism of Action", Regulation of Angiogenesis, I.D. Goldberg and E.M. Rosen (eds.), 79, 1997, pp. 159-192.
Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, Jan. 2001, pp. 1848-1853.
Kwok, C., et al., "Design of Infection-Resistant Antibiotic-Releasing Polymers: I. Fabrication and Formulation", Journal of Controlled Release, 62, 1999, pp. 289-299.

Laboratory of Liposome Research, "Liposomes: General Properties", downloaded from the Internet on Feb. 9, 2006 at: http://www.unizh.ch/onkwww/lipos.htm, 5 pages.
Laham, R. J., "Intrapericardial Delivery of Fibroblast Growth Factor-2 Induces Neovascularization in a Porcine Model of Chronic Myocardial Ischemia", J. Pharmacol Exper Therap, 292(2), 2000, pp. 795-802.
Leibovich, S. J., et al., "Macrophage-Induced Angiogenesis is Mediated by Tumour Necrosis Factor-α", Nature, vol. 329, Oct. 15, 1987, pp. 630-632.
Leor, J., et al., "Bioengineered Cardiac Grafts-A New Approach to Repair the Infarcted Myocardium?", Circulation, 102[suppl III], 2000, pp. 111-56-111-61.
Leor, J., et al., "Gene Transfer and Cell Transplant: An Experimental Approach to Repair a 'Broken Heart'", Cardiovascular Research, 35, 1997, pp. 431-441.
Leroux, J. C., et al., "An Investigation on the Role of Plasma and Serum Opsonins on the Internalization of Biodegradable poly(D,L-lactic acid) Nanoparticles by Human Monocytes", Life Sci., 57(7), Abstract downloaded from the Internet at: http://www.ncbi.nlm.nih.gov/entrez/query.fcgi?cmd=Retrieve&db=pubmed, 1 page, 1995, pp. 695-703.
Lewin, B., "Repressor is Controlled by a Small Molecule Inducer", Genes VII, Oxford University Press, $7^{th}$ ed., 2000, pp. 277-280.
Li, et al., "Cell Therapy to Repair Broken Hearts", Can. J. Cardiol., vol. 14, No. 5, May 1998, pp. 735-744.
Li, W. W., et al., "Lessons to be Learned from Clinical Trials of Angiogenesis Modulators in Ischemic Diseases", Angiogenesis in Health & Disease: Basic Mechanisms and Clinical Applications, Rubanyi, G. (ed), Marcel Dekker, Inc. New York, 2000, Chapter 33.
Li, J., et al., "PR39, A Peptide Regulator of Angiogenesis", Nature Medicine, 6(1), Jan. 2000, pp. 49-55.
Li., Y. Y., et al., "Differential Expression of Tissue Inhibitors of Metalloproteinases in the Failing Human Heart", Circulation, 98(17), 1998, pp. 1728-1734.
Lindsey, M., et al., "Selective Matrix Metalloproteinase Inhibition Reduces Left Ventricular Remodeling but does not Inhibit Angiogenesis after Myocardial Infarction", Circulation, 105(6), 2002, pp. 753-758.
Long, D. M., et al., "Self-Cleaving Catalytic RNA", FASEB Journal, 7, 1993, pp. 25-30.
Lopez, J. J., et al., "VEGF Administration in Chronic Myocardial Ischemia in Pigs", Cardiovasc. Res., 40(2), Abstract downloaded from the Internet at: http://www.ncbi.nlm.nih.gov/entrez/query.fcgi?cmd=Retrieve&db=pubmed, 1 page, 1998, pp. 272-281.
Lu, L., et al., "Biodegradable Polymer Scaffolds for Cartilage Tissue Engineering", Clinical Orthopaedics and Related Research, Carl T. Brighton (ed.). No. 391S, 2001, pp. S251-270.
Luo, Y., et al., "Cross-linked Hyaluronic Acid Hydrogel Films: New Biomaterials for Drug Delivery", Journal of Controlled Release, 69, 2000, pp. 169-184.
Lutolf, M., et al., "Synthesis and Physicochemical Characterization of End-Linked Poly(ethylene glycol)-co-peptide Hydrogels Formed by Michael-Type Addition", Biomacromolecules, vol. 4, 2003, pp. 713-722.
Lyman, M. D., et al., "Characterization of the Formation of Interfacially Photopolymerized Thin Hydrogels in Contact with Arterial Tissue", Biomaterials, 17(3), 1996, pp. 359-364.
Mansour, S., et al., "Disruption of the proto-oncogene int-2 in mouse embryo-derived stem cells: A general strategy for targeting mutations to non-selectable genes", Nature, 336, 1988, pp. 348-352.
Martin, S. L., et al., "Total Synthesis and Expression in *Escherichia Coli* of a Gene Encoding Human Tropoelastin", Gene, 1995, Abstract, 1 page.
McDevitt, T., et al., "In vitro Generation of Differentiated Cardiac Myofibers on Micropatterned Laminin Surfaces", J. Biomed Mater Res., 60, 2002, pp. 472-479.
Meinel, L., et al., "The Inflammatory Responses to Silk Films in Vitro and in Vivo", Biomaterials, vol. 26, 2005, pp. 147-155.
Narmoneva, D. A., et al., "Self-assembling short oligopeptides and the promotion of angiogenesis", Biomaterials, 26, 2005, pp. 4837-4846.

(56) References Cited

OTHER PUBLICATIONS

Nazarov, R., et al., "Porous 3-D Scaffolds from Regenerated Silk Fibroin", Biomacromolecules, vol. 5(3), 2004, pp. 718-726.
Nguyen, K. T., et al., "Photopolymerizable Hydrogels for Tissue Engineering Applications", Biomaterials, 23, 2002, pp. 4307-4314.
Nikolic, S. D., et al., "New Angiogenic Implant Therapy Improves Function of the Ischemic Left Venticle", Supplement to Circulation; Abstracts From Scientific Sessions 2000, 102(18), Oct. 2000, pp. 11-689, Abstract 3331.
Nitinol Technical Information, "NiTi Smart Sheets", downloaded from the Internet on Dec. 10, 2002 at: http://www.sma-inc.com/information.html, 1 page.
Nose, et al., "A novel cadherin cell adhesion molecule: its expression patterns associated with implantation and organogenesis of mouse embryos", Journal of Cell Biology, vol. 103 (No. 6, Pt. 2), The Rockefeller University Press, Dec. 1986, pp. 2649-2658.
Ohyanagi, H., et al., "Kinetic Studies of Oxygen and Carbon Dioxide Transport into or from Perfluorochemical Particles", Proc. ISAO, vol. 1 (Artificial Organs vol. 2 (Suppl.)), 1977, pp. 90-92.
Ozbas, B., et al., "Salt-Triggered Peptide Folding and Consequent Self-Assembly into Hydrogels with Tunable Modulus", Macromolecules, 37(19), 2004, pp. 7331-7337.
Ozbas-Turan, S., "Controlled Release of Interleukin-2 from Chitosan Microspheres", Journal of Pharmaceutical Sciences, 91(5), May 2002, pp. 1245-1251.
Palmiter, R., et al., "Germ-Line Transformation of Mice", Ann. Rev. Genet., 20, 1986, pp. 465-499.
Patrick, C. R., "Mixing and Solution Properties of Organofluorine Compounds", Preparation, Properties and Industrial Applications of Organofluorine Compounds, Chapter 10, R.E. Banks (ed.), 1$^{st}$ edition, Ellis-Horwood Ltd., Chichester:England, 1982, pp. 323-342.
Peattie, R. A., et al., "Stimulation of in Vivo Angiogenesis by Cytokine-Loaded Hyaluronic Acid Hydrogel Implants", Biomaterials, 25(14), Abstract downloaded from: www.sciencedirect.com, Jun. 2004, 2 pages.
Penta, K., et al., "Dell Induces Integrin Signaling and Angiogenesis by Ligation of aVβ3", J. Biolog. Chem., 274(16), Apr. 1999, pp. 11101-11109.
Perin, E. C., et al., "Transendocardial, Autologous Bone Marrow Cell Transplantation for Severe, Chronic, Ischemic Heart Failure", Circulation, 2003, 1 page.
Pouzet, B., et al., "Is Skeletal Myoblast Transplantation Clinically Relevant in the Era of Angiotensin-Converting Enzyme Inhibitors?", Circulation, 104 [suppl 1], Sep. 2001, pp. I-223-I-228.
Prather, et al., "Nuclear Transplantation in Early Pig Embryos", Biol. Reprod., 41, 1989, pp. 414-418.
Prosci Incorporated, "ILPIP (CT) Peptide", 1 page.
Quellec, P., et al., "Protein Encapsulation Within Polyethylene Glycol-coated Nanospheres. 1. Physicochemical Characterization", J. Biomed. Mater. Res., 42(1), 1998, Abstract, 1 page.
Ramirez-Solis, R., et al., "Gene Targeting in Embryonic Stem Cells", Methods in Enzymology, 225, 1993, pp. 855-878.
Sawhney, A. S., et al., "Bioerodible Hydrogels Based on Photopolymerized Poly(ethylene glycol)-co-poly(a-hydroxy acid) Diacrylate Macromers", Macromolecules, 26(4), 1993, pp. 581-587.
Sbaa-Ketata, E., et al., "Hyaluronan-Derived Oligosaccharides Enhance SDF-1-Dependent Chemotactic Effect on Peripheral Blood Hematopoietic CD34+ Cells", Stem Cells, 20(6), Letter to the Editor downloaded from the Internet at: http://stemcells.alphamedpress.org/cgi/content/full/20/6/585, 2002, pp. 585-587.
Segura, T., et al., "Crosslinked Hyaluronic Acid Hydrogels: A Strategy to Functionalize and Pattern", Biomaterials, vol. 26(4), Feb. 2005, pp. 359-371.
Segura, T., et al., "DNA delivery from hyaluronic acid-collagen hydrogels via a substrate-mediated approach", Biomaterials, vol. 26, 2005, pp. 1575-1584.
Segura, T., et al., "Substrate-Mediated DNA Delivery: Role of the Cationic Polymer Structure and Extent of Modification", Journal of Controlled Release, 93, 2003, pp. 69-84.
Segura, T., et al., "Surface-Tethered DNA Complexes for Enhanced Gene Delivery", Bioconjugate Chem, 13(3), 2002, pp. 621-629.
Shibasaki, F., et al., "Suppression of Signalling Through Transcription Factor NF-AT by Interactions Between Calcineurin and Bcl-2", Nature, 386(6626), Abstract downloaded from the Internet at: http://www.ncbi.nlm.nih.gov/entrez/query.fcgi?CMD=Text&DB=pubmed, 1 page, 1997.
Shin, H., et al., "Attachment, Proliferation, and Migration of Marrow Stromal Osteoblasts Cultured on Biomimetic Hydrogels Modified with an Osteopontin-Derived Peptide", Biomaterials, 25, 2004, pp. 895-906.
Shin, H., et al., "In vivo bone and soft tissue response to injectable, biodegradable oligo(poly(ethylene glycol) fumarate) hydrogels", Biomaterials 24, Elseview Science Ltd., 2003, pp. 3201-3211.
Shu, Z., et al., "Disulfide-crosslinked hyaluronan-gelatin hydrogel films: A covalent mimic of the extracellular matrix for in vitro cell growth", Biomaterials, vol. 24(21), Sep. 2003, pp. 3825-3834.
Shu, Zheng, et al., "In situ crosslinkable hyaluronan hydrogels for tissue engineering", Biomaterials, vol. 25, 2004, pp. 1339-1348.
Spinale, F. G., "Matrix Metalloproteinases—Regulation and Dysregulation in the Failing Heart", Circ. Res., 90, 2002, pp. 520-530.
Springer, M., et al., "Angiogenesis Monitored by Perfusion with a Space-Filling Microbead Suspension", Mol. Ther., 1(1), Abstract downloaded from the Internet at: http://www.ncbi.nlm.nih.gov/entrez/query.fcgi?cmd=Retrieve&db=PubMed, 1 page, 2000, pp. 82-87.
Storm, G., et al., "Surface Modification of Nanoparticles to Oppose Uptake by the Mononuclear Phagocyte System", Advanced Drug Delivery Reviews, 17(1), Abstract downloaded from the Internet at: http://www.sciencedirect.com, 1 page, Oct. 1995, pp. 31-48.
Strauer, B., et al., "Repair of Infarcted Myocardium by Autologous Intracoronary Mononuclear Bone Marrow Cell Transplantation in Humans", Circulation, 106, 2002, pp. 1913-1918.
Tybulewicz, V., et al., "Neonatal lethality and lymphopenia in mice with a homozygous disruption of the c-abl proto-oncogene", Cell, 65(7), Abstract downloaded from the Internet at: http://www.sciencedirect.com, 2 pages, Jun. 1991, pp. 1153-1163.
Unger, E. F., et al., "Effects of a Single Intracoronary Injection of Basic Fibroblast Growth Factor in Stable angina Pectoris", Am. J. Cardiol., 85(12), Abstract downloaded from the Internet at: http://www.sciencedirect.com, 2 pages, Jun. 2000, pp. 1414-1419.
Van Luyn, M. J., et al., "Cardiac Tissue Engineering: Characteristics of in Unison Contracting Two- and Three-Dimensional Neonatal Rat Ventricle Cell (Co)-Cultures", Biomaterials, 23, 2002, pp. 4793-4801.
Vercruysse, K. P., et al., "Synthesis and in Vitro Degradation of New Polyvalent Hydrazide Cross-Linked Hydrogels of Hyaluronic Acid", *Bioconjugated Chem*, 8(5), Abstract downloaded from the Internet at: http://pubs.acs.org/cgi-bin/abstract.cgi/bcches/1997/8/i05/abs/bc9701095.html, 1 page, (1997) pp. 686-694.
Vlodavsky, I., et al., "Extracellular Matrix-resident Basic Fibroblast Growth Factor: Implication for the Control of Angiogenesis", J. Cell Biochem, 45(2), Abstract downloaded from the Internet at: http://www.ncbi.nlm.nih.gov/entrez/guery.fcgi?cmd=Retrieve&db=PubMed, 1 page, Feb. 1991, pp. 167-176.
Wang, M., et al., "Mechanical Properties of Electrospun Silk Fibers", Macromolecules, vol. 37(18), 2004, pp. 6856-6864.
Wasielewski, "Ischamische Erkrankungen, Gefassneubildung anregen", Deutsche Apotheker Zeitung, vol. 140, No. 3, Stuttgart (DE), Jan. 20, 2000, pp. 232-233.
Wilensky, R., et al., "Direct intraarterial wall injection of microparticles via a catheter: A potential durg delivery strategy following angioplasty", American Heart Journal, 122, 1991, pp. 1136.
Witzenbichler, B., et al., "Vascular Endothelial Growth Factor-C (VEGF-C/VEGF-2) Promotes Angiogenesis in the Setting of Tissue Ischemia", Am Pathol., 153(2), Aug. 1998, pp. 381-394.
Yager, P., et al., "Silk Protein Project", www.faculty.washington.edu/yagerp/silkprojecthome.html, Aug. 23, 199) 18 pages
Yamamoto, N., et al., "Histologic evidence that basic fibroblast growth factor enhances the angiogenic effects of transmyocardial laser revascularization", Basic Research in Cardiology, vol. 95, No. 1, Feb. 1, 2000, pp. 55-63.

(56) References Cited

OTHER PUBLICATIONS

Yeo, L.Y., et al., "AC Electrospray Biomaterials Synthesis", Biomaterials, 2005, 7 pages.
Zervas, L., et al., "On Cysteine and Cystine Peptides. II. S-Acylcysteines in Peptide Synthesis", J. Am. Chem. Soc., 85(9), May 1963, pp. 1337-1341.
Zheng, W., et al., "Mechanisms of coronary angiogenesis in response to stretch: role of VEGF and TGF-beta", Am J Physiol Heart Circ Physiol., 280(2), Feb. 2001, pp. H909-H917.
Zimmermann, W., et al., "Engineered Heart Tissue for Regeneration of Diseased Hearts", Biomaterials, 25, 2004, pp. 1639-1647.
Anderson, James M., et al., "Biodegradation and biocompatibility of PLA and PLGA microspheres", *Advanced Drug Delivery Reviews 28*, (1997),5-24.
Buschmann, I , et al., "Arteriogenesis versus angiogenesis: Two mechanisms of vessel growth", *News Physiol. Sci.*, vol. 14, (Jun. 1999),121-125.
Caplan, Michael J., et al., "Dependence on pH of polarized sorting of secreted proteins", *Dept. of Cell Biology and Dept. of Pathology, Yale Universit School of Medicine, Nature* vol. 329, (Oct. 15, 1987),630.
Helisch, A , et al., "Angiogenesis and arteriogenesis—not yet for prescription", *NEUE Diagnostische Und Therap. Verfahren Z Kardiol 89*, (2000),239-244.
Ito, Wulf D., et al., "Monocyte chemotactic protein-1 increases collateral and peripheral conductance after femoral artery occlusion", *Max-Planck-Institute for Physiological and Clinical Research*, Bad Nauheim, Germany, (Feb. 21, 1997),829-837.
Kalltorp, Mia , et al., "Inflammatory cell recruitment, distribution, and chemiluminescence response at IgG precoated- and thiol functionalized gold surfaces", *Swedish Biomaterials Consortium, Swedish Foundation for Strategic Research*, Apr. 9, 1999 ,251-259.
Kawai, Katsuya , et al., "Accelerated Tissue Regeneration Through Incorporation of Basic Fibroblast Growth Factor-Impregnated Gelatin Microspheres into Artificial Dermis", *Biomaterials 21*, (2000),489-499.
Kipshidze, Nicholas , et al., "Therapeutic angiogenesis for critical limb ischemia to limit or avoid amputation", *University of Wisconsin Medical School, The Journal of Invasive Cardiology*, vol. 11, No. 1, (Jan. 1999),25-28.
Klugherz, Bruce D., et al., "Gene delivery from a DNA controlled-release stent in procine coronary arteries", *Nature Biotechnology*, vol. 18, (Nov. 2000),1181-1184.
Kohilas, K , et al., "Effect of prosthetic titanium wear debris on mitogen-induced monocyte and lymphoid activation", *John Hopkins University, Dept. of Orthopaedic Surgery*, (Apr. 1999) ,95-103.
Leibovich, S. Joseph , et al., "Macrophage-induced angiogenesis is mediated by tumour necrosis factor-alpha", *Depts. of Oral Biology and Pathology, Northwestern University Dental School, Nature*, vol. 329. (Oct. 15, 1997),630-633.
Lopez, John J., et al., "Angiogenic potential of perivascular delivered aFGF in a porcine model of chronic myocardial ischemia", *The American Physiological Society*, 0363-6135/98, (1998),H930-H936.
Nikolic, Serjan D., et al., "Novel means to improve coronary blood flow", *Clinical Science, Abstracts from Scientific Sessions*, (2000),II-689.
Rowley, Jon A., et al., "Alginate Hydrogels as Synthetic Extracelllular Matrix Materials", *Biomaterials 20*, 45-53.
Simons, Michael , et al., "Clinical trials in coronary angiogenesis: Issues, problems, consensus, An expert panel summary", *Angiogenesis, Research Center, American Heart Association, Inc.*, (Sep. 12, 2000),1-14.
Spenlehauer, G , et al., "In vitro and in vivo degradation of poly(D,L lactide/glycolide) type microspheres made by solvent evaporation method", Biomaterials, vol. 10, (Oct. 1989),557-563.
Van Der Giessen, Willem J., et al., "Marked inflammatory sequelae to implantation of biodegradable and nonbiodegradable polymers in porcine coronary arteries", *Dept. of Cardiology, Erasmus University Rotterdam, Circulation*, vol. 94, No. 7, (Oct. 1, 1996),1690-1697.

Visscher, G.E. , et al., "Tissue response to biodegradable injectable microcapsules", *Journal of Biomaterials Applications*, vol. 2 (Jul. 1987),118-119.
Abbott Cardiovascular Systems, Non Final Office Action dated Apr. 6, 2009 for U.S. Appl. No. 11/447,340.
Abbott Cardiovascular Systems, Non Final Office Action dated Apr. 13, 2009 for U.S. Appl. No. 11/566,643.
Abbott Cardiovascular Systems, Non Final Office Action dated Apr. 29, 2009 for U.S. Appl. No. 12/013,286.
Abbott Cardiovascular Systems, Non Final Office Action dated May 12, 2009 for U.S. Appl. No. 11/496,824.
Abbott Cardiovascular Systems, Non Final Office Action dated Mar. 13, 2009 for U.S. Appl. No. 10/414,602.
Abbott Cardiovascular Systems, International search report and written opinion dated Jun. 18, 2009 for PCT/US2008/051505.
Abbott Cardiovascular Systems, Non Final Office Action dated Jul. 9, 2009 for U.S. Appl. No. 11/561,328.
Elbert, D. L., et al., "Protein delivery from materials formed by self-selective conjugate addition reactions", Journal of Controlled Release, 76, (2001), 11-25.
Staatz, WD , et al., "Identification of a tetrapeptide recognition sequence for the alpha 2 beta 1 integrin in collagen", Journal of Biological Chemistry, 1991, 266(12), pp. 7363-7367.
Abbott Cardiovascular Systems, International Preliminary Report on Patentability dated Jul. 30, 2009 for PCT/US2008/051505.
Abbott Cardiovascular Systems, Final office action dated Nov. 12, 2009 for U.S. Appl. No. 12/013,286.
Abbott Cardiovascular Systems, Final office action dated Nov. 25, 2009 for U.S. Appl. No. 11/566,643.
Abbott Cardiovascular Systems, Non final office action dated Dec. 9, 2009 for U.S. Appl. No. 10/781,984.
Abbott Cardiovascular Systems, Examination Report dated Jan. 13, 2010 for EP Application No. 07795729.8.
Abbott Cardiovascular Systems, Non final office action dated Feb. 5, 2010 for U.S. Appl. No. 11/447,340.
Abbott Cardiovascular Systems, Examination Report dated Jan. 15, 2010 for EP 08727952.7.
Abbott Cardiovascular Systems, Examination Report dated Feb. 5, 2010 for EP 07810637.4.
Zheng, Shu , et al., "In situ crosslinkable hyaluronan hydrogels for tissue engineering", Biomaterials, Elsevier Science Publishers, vol. 25, No. 7-8, (2004), 1339-1348.
Abbott Cardiovascular Systems Inc., Non final office action dated Apr. 14, 2010 for U.S. Appl. No. 12/016,180.
Hao, et al., "Angiogenic effects of sequential release of VEGF-A16 and PDGF-BB with alginate hydrogels after myocardial infarction," Cardiovascular Research 75 (2007) 178-185.
Abbott Cardiovascular Systems, Final office action dated Apr. 22, 2010 for U.S. Appl. No. 10/414,602.
Abbott Cardiovascular Systems, Non-Final Office Action dated Jun. 4, 2010 for U.S. Appl. No. 10/781,984.
Abbott Cardiovascular Systems, Final Office Action Mailed Jun. 11, 2010 for U.S. Appl. No. 11/561,328.
Ritter, A. B., et al., "Elastic modulus, distensibility, and compliance (capacitance)", Biomedical Engineering Principles, Chapter 4, (2005), 187-191.
Abbott Cardiovascular Systems, Non final office action dated Aug. 5, 2009 for U.S. Appl. No. 11/031,608.
Abbott Cardiovascular Systems, Final office action dated Mar. 29, 2010 for U.S. Appl. No. 11/031,608.
Abbott Cardiovascular Systems, Non final office action dated Aug. 13, 2010 for U.S. Appl. No. 11/447,340.
Abbott Cardiovascular Systems, Final office action mailed Sep. 27, 2010 for U.S. Appl. No. 12/016,180.
Abbott Cardiovascular Systems, Final Office Action mailed Nov. 22, 2010 for U.S. Appl. No. 10/781,984., 13 pages.
Abbott Cardiovascular Systems, Non-final Office Action mailed Nov. 24, 2010 for US 12/013,286., 11 pages.
Abbott Cardiovascular Systems, Non-final Office Action mailed Dec. 8, 2010 for U.S. Appl. No. 11/566,643., 17 pages.
Abbott Cardiovascular Systems, Non-final Office Action mailed Dec. 10, 2010 for U.S. Appl. No. 11/938,752., 32 pages.

(56) References Cited

OTHER PUBLICATIONS

Abbott Cardiovascular Systems, Non-final Office Action mailed Dec. 17, 2010 for U.S. Appl. No. 11/933,922, 23 pages.
Abbott Cardiovascular Systems, website for HEALON (R) OVD, copyright 2010, accessed Dec. 15, 2010, URL: <http://abbottmedicaloptics.com/products/cataract/ovds/healon-viscoelastic>, 2010 2 pages.
Abbott Cardiovascular Systems, Product Information Sheet for HEALON (R), from Abbott Medical Optics, (2005), 1 page.
Haynesworth, Stephen E., et al., "Platelet Effects on Human Mesenchymal Stem Cells", Abstract, presented at Orthopaedic Research Society 48th Annual Meetin Dallas, TX, Oct. 13, 2010, 2 pages.
Abbott Cardiovascular Systems, Japanese Office Action dated Dec. 8, 2010 for Japanese Patent App No. 2006-509975.
Abbott Cardiovascular Systems, Final Office Action mailed Apr. 15, 2011 for U.S. Appl. No. 10/414,602.
Advanced Cardiovascular Systems, Extended European search report dated Apr. 21, 2011 for EP Application No. 10186186.2.
Advanced Cardiovascular Systems, Extended EP Search Report dated May 20, 2011 for EP Application No. 10186197.9.
Chung, Y., et al., "Sol-gel transition temperature of PLGA-g-PEG aqueous solutions", Biomacromolecules, vol. 3, No. 3, (May 2002), 511-516.
Abbott Cardiovascular Systems, Non final Office action mailed Jun. 7, 2011 for U.S. Appl. No. 11/447,340.
Abbott Cardiovascular Systems, Non final office action mailed Jul. 6, 2011 U.S. Appl. No. 10/781,984.
Abbott Cardiovascular Systems, Final office action mailed Jul. 18, 2011 for U.S. Appl. No. 11/566,643.
Abbott Cardiovascular Systems, Non-Final Office Action mailed Aug. 31, 2010 for U.S. Appl. No. 11/110,223.
Abbott Cardiovascular Systems, Final office action mailed Sep. 20, 2011 for U.S. Appl. No. 11/938 752.
Abbott Cardiovascular Systems, Final Office Action mailed Oct. 21, 2011 for U.S. Appl. No. 10/781,984, 10 pages.
Abbott Cardiovascular Systems, Final Office Action mailed Jan. 5, 2011 for U.S. Appl. No. 11/361,920, 13 pages.
Abbott Cardiovascular Systems, Office Action mailed Jan. 17, 2012 for European Patent Application 08727952.7, 6 pages.
Abbott Cardiovascular Systems, Non-Final Office Action mailed Mar. 5, 2009 for U.S. Appl. No. 11/507,860.
Abbott Cardiovascular Systems, Final Office Action mailed Jul. 15, 2010 for U.S. Appl. No. 11/507,860.
Abbott Cardiovascular Systems, Non-Final Office Action mailed Jan. 30, 2012 for U.S. Appl. No. 10/781,984.
Abbott Cardiovascular Systems, Final Office Action mailed Feb. 8, 2012 for Japanese application No. 2006-509975.
Abbott Cardiovascular Systems, Non-Final Office Action mailed Feb. 15, 2012 for U.S. Appl. No. 12/114,717.
Abbott Cardiovascular Systems, European Office Action mailed Apr. 11, 2012 for App No. 12155231.9, 9 pages.
Abbott Cardiovascular Systems, European Office Action mailed Apr. 10, 2012 for App No. 07810637.4, 6 pages.
Abbott Cardiovascular Systems, Final Office Action mailed May 9, 2012 for U.S. Appl. No. 11/110,223.
Abbott Cardiovascular Systems, European Search report for application No. 12151788.2 mailed Apr. 18, 2012, 6 pages.
Abbott Cardiovascular Systems, Non-final Office Action mailed Jun. 26, 2012 for U.S. Appl. No. 12/632,612.
Abbott Cardiovascular Systems, Japanese Office Action dated Jun. 11, 2012 for Appln. No. 2010-162711.
Bull, S., et al., "Self-Assembled Peptide Amphiphile Nanofibers Conjugated to MRI Contrast Agents", Nano Letters, vol. 5, No. 1, (Jan. 2005), 4 pages.
Csonka, E., et al., "Interspecific Interaction of Aortic Endothelial and Smooth Muscle Cells", Acta Morphologica Hungarica, vol. 35, No. 1-2, (1987), 31-35.
Griese, D. P., et al., "Vascular gene delivery of anticoagulants by transplantation of retrovirally-transduced endothelial progenitor cells", Cardiovascular Research, vol. 58, (2003), 469-477.
Hartgerink, J. D., et al., "Peptide-amphiphile nanofibers: A versatile scaffold for the preparation of self-assembling materials", PNAS, vol. 99, No. 8, (Apr. 16, 2002), 5133-5138.
Hartgerink, J. D., et al., "Self-Assembly and Mineralization of Peptide-Amphiphile Nanofibers", Science, vol. 294, (Nov. 23, 2001), 1684-1688.
Li, B., et al., "VEGF and PlGF promote adult vasculogenesis by enhancing EPC recruitment and vessel formation at the site of tumor neovascularization", The FASEB Journal, vol. 20, (2006), 1495-1497.
Seeger, J. M., et al., "Improved in vivo endothelialization of prosthetic grafts by surface modification with fibronectin", J Vasc Surg, vol. 8, No. 4, (Oct. 1988), 476-82 (Abstract only).
Urbich, C., et al., "Endothelial Progenitor Cells: Characterization and Role in Vascular Biology", Circulation Research, vol. 95, (2004), 343-353.
Abbott Cardiovascular Systems, Japanese office action dated Aug. 20, 2012 for JP 2009-537153.
Abbott Cardiovascular Systems, Non-Final Office Action dated Oct. 3, 2012 for U.S. Appl. No. 12/756,119.
Abbott Cardiovascular Systems, Japanese Office Action dated Aug. 27, 2012 for JP 2009-522776.
Abbott Cardiovascular Systems, Final Office Action dated Nov. 8, 2012 for U.S. Appl. No. 12/114,717.
Abbott Cardiovascular Systems, Final Office Action mailed Nov. 7, 2012 for U.S. Appl. No. 10/781,984.
Abbott Cardiovascular Systems, Japanese Office Action dated Nov. 19, 2012 for JP 2009-539265.
Davis, M. E., et al., "Injectable Self-Assembling Peptide Nanofibers Create Intramyocardial Microenvironments for Endothelial Cells", Circulation, 111, (2005), 442-450.
Hao, X, et al., "Angiogenic Effects of Sequential release of VEGF-A 165 and PDGF-BB with Alginate Hydrogels After Myocardial Infarction", Cardiovascular Research, 75(1), (Apr. 6, 2007), 178-185.
Mogan, L., "Rationale of platelet gel to augment adaptive remodeling of the injured heart", J Extra Corpor Technol, 36(2), (Jun. 2004), 191-196.

* cited by examiner

METHOD FOR INTRAVASCULAR DELIVERY OF A TREATMENT AGENT BEYOND A BLOOD VESSEL WALL

CROSS-REFERENCE TO RELATED APPLICATION

This application is a continuation-in-part of U.S. patent application Ser. No. 10/011,071 filed Nov. 30, 2001 now U.S. Pat. No. 6,702,744.

BACKGROUND

1. Field

Resolving ischemia by inducing formation of blood vessels through therapeutic angiogenesis and/or therapeutic angiomyogenesis.

2. Relevant Art

A major component of morbidity and mortality attributable to cardiovascular disease occurs as a consequence of the partial or complete blockage of vessels carrying blood in the coronary and/or peripheral vasculature. When such vessels are partially occluded, lack of blood flow causes ischemia to the muscle tissues supplied by such vessel, consequently inhibiting muscle contraction and proper function. Total occlusion of blood flow causes necrosis of the muscle tissue.

Blood vessel occlusions are commonly treated by mechanically enhancing blood flow in the affected vessels. Such mechanical enhancements are often provided by employing surgical techniques that attach natural or synthetic conduits proximal and distal to the areas of occlusion, thereby providing bypass grafts, or revascularization by various means to physically enlarge the vascular lumen at the site of occlusion. These revascularization procedures involve such devices as balloons, endovascular knives (atherectomy), and endovascular drills. The surgical approach is accompanied by significant morbidity and even mortality, while the angioplasty-type processes are complicated by recurrent stenoses in many cases.

In some individuals, blood vessel occlusion is partially compensated by natural processes, in which new vessels are formed (termed "angiogenesis") and small vessels are enlarged (termed "arteriogenesis") to replace the function of the impaired vessels. These new conduits may facilitate restoration of blood flow to the deprived tissue, thereby constituting "natural bypasses" around the occluded vessels. However, some individuals are unable to generate sufficient collateral vessels to adequately compensate for the diminished blood flow caused by cardiovascular disease. Accordingly, it would be desirable to provide a method and apparatus for delivering agents to help stimulate the natural process of therapeutic angiogenesis to compensate for blood loss due to an occlusion in a coronary and peripheral arteries in order to treat ischemia.

Myocardial infarction (MI) is one form of heart disease that often results from the sudden lack of supply of oxygen and other nutrients. The lack of blood supply is a result of closure of the coronary artery that nourishes a particular part of the heart muscle. The cause of this event is generally caused by arteriosclerosis "hardening of the arteries" in coronary vessels.

Formerly, it was believed that an MI was caused from a slow procession of closure from, for example, 95 percent then to 100 percent but an MI can also be a result of minor blockages where, for example, there is rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Even though relatively effective systemic drugs exist to treat MI such as ACE-inhibitors and Beta-blockers, a significant portion of the population that experiences a major MI ultimately develop heart failure. An important component in the progression to heart failure is remodeling of the heart due to mechanical forces resulting in uneven stress and strain distribution in the left ventricle. Once an MI occurs remodeling of the heart begins. The principal components of the remodeling event include myocyte death, edema and inflammation, followed by fibroblast infiltration and collagen deposition, and finally scar formation. The principal component of the scar is collagen. Since mature myocytes of an adult are not regenerated the infarct region experiences significant thinning. Myocyte loss is the major etiologic factor of wall thinning and chamber dialation that may ultimately lead to progression of cardiac myopathy. Myocyte death can and does occur. In other areas, remote regions experience hypertrophy (thickening) resulting in an overall enlargement of the left ventricle. This is the end result of the remodeling cascade. These changes in the heart result in changes in the patient's lifestyle and their ability to walk and to exercise. These changes also correlate with physiological changes that result in increase in blood pressure and worsening systolic and diastolic performance. Accordingly, it would be desirable to provide a method and apparatus for delivery agents that stabilize a ventricle (e.g., the left ventricle) and/or stimulate muscle cell growth.

SUMMARY

A method is disclosed. In one embodiment the method includes positioning a delivery device such as a catheter at a location in a blood vessel and advancing the delivery device a distance into a wall of the blood vessel to a treatment site. A treatment agent including a cellular component is then introduced through the delivery device to the treatment site. Suitable treatment agents, such as bone marrow cells, can induce an angiogenic response when delivered into ischemic tissue. Other cells (e.g., stem cells) can also induce an angiomyogenesic response when delivered into ischemic tissue such as the tissue of the left ventricle. Angiomyogenesis can stimulate myocyte growth and reduce or inhibit, for example, myocyte depletion following an MI. The treatment agent may be introduced in the form of or in conjunction with a matrix or gel that may serve to retain the treatment agent at or near a treatment site or region of interest. Alternatively, a matrix or gel may be formed in situ.

The method also includes identifying a treatment site based on imaging a thickness of a portion of the wall of the blood vessel. In the example of introducing a treatment agent that would stimulate a therapeutic angiogenesis response, the method describes a technique for accurately delivering a treatment agent into the wall of the blood vessel or beyond the wall of the blood vessel as the particular situation may dictate. The method utilizes imaging of a thickness of the wall of a blood vessel to accurately place the treatment agent. Suitable imaging techniques include, but are not limited to, ultrasonic imaging, optical imaging, and magnetic resonance imaging.

In another embodiment, a composition is disclosed. The composition includes a treatment agent including a cellular component associated with a matrix material. The composition is suitable for transvascular (e.g., percutaneous) delivery. The cellular component may include adult or embryonic stem cells. Such cells may be transfected with a gene vector, such as a growth factor that may upregulate angiogen production. The matrix material, in one embodiment, is a material that by itself or with an interaction or a reaction with another component forms a matrix or gel (e.g., a hydrogel). Alternatively, the matrix material itself may be a gel particle, such as a porous gel particle including the treatment agent.

In another embodiment, an apparatus is described that allows the accurate introduction of a treatment agent in or around a blood vessel. The apparatus includes, for example, an expandable body such as a catheter balloon having dimensions suitable for percutaneous delivery and a plurality of delivery cannulas connected to the expandable body dilatable balloon assembly connected to the catheter body comprising a balloon having a proximal wall. The apparatus also includes a plurality of needles disposed in respective ones of the plurality of delivery cannulas. Each needle has a length such that, in a deployed position, the needles extend from a distal end of respective ones of the plurality of delivery cannulas. The plurality of delivery cannulas are connected to the expandable body such that, in a deployed position, a delivery of one of the needles is adjacent a delivery end of another needle. In this manner, a composition that includes a treatment agent including a cellular component that is intended to be a part of a matrix or gel formed in situ can be introduced in two parts (e.g., co-injected) with material from each needle being delivered, perhaps simultaneously, at a designated treatment site.

The apparatus may also include an imaging cannula or body disposed within the catheter body and comprising a lumen having a dimension suitable for a portion of an imaging device to be advanced therethrough. In another embodiment, the apparatus further includes a portion of an imaging device disposed within the imaging lumen adapted to generate imaging signals of the blood vessel, including imaging signals of a thickness of the wall of a blood vessel. An apparatus such as described is suitable for accurately introducing a treatment agent at a desired treatment site in or around a blood vessel including peripheral to a blood vessel.

In a further embodiment, a kit is described. A suitable kit may include a composition including a treatment agent including a cellular component, for example, in a targeted dose to induce or modulate therapeutic angiogenesis or therapeutic angiomyogenesis. A kit may also include a first composition and a second composition where, for example, the first composition and the second composition may be introduced percutaneously (e.g., in a form or transformable to a form that may be introduced through one or more needle catheters) to form a matrix or gel in vivo.

BRIEF DESCRIPTION OF THE DRAWINGS

The features of the described embodiments are specifically set forth in the appended claims. However, the embodiments are best understood by referring to the following description and accompanying drawings, in which similar parts are identified by like reference numerals.

DETAILED DESCRIPTION

In connection with the description of the various embodiments, the following definitions are utilized:

"Therapeutic angiogenesis" refers to the processes of causing or inducing angiogenesis and arteriogenesis.

"Angiogenesis" is the promotion or causation of the formation of new blood vessels in the ischemic region.

"Arteriogenesis" is the enlargement of pre-existing collateral vessels. The collateral vessels allow blood to flow from a well-perfused region of the vessel into the ischemic region.

"Therapeutic angiomyogenesis" refers to the process of causing or inducing angiomyogenesis.

"Angiomyogenesis" is the promotion or causation of myocytes.

"Ischemia" is a condition where oxygen demand of the tissue is not met due to localized reduction in blood flow caused by narrowing or occlusion of one or more vessels. Narrowing of arteries such as coronary arteries or their branches, is most often caused by thrombosis or via deposits of fat, connective tissue, calcification of the walls, or restenosis due to abnormal migration and proliferation of smooth muscle cells.

"Occlusion" is the total or partial obstruction of blood flow through a vessel.

"Treatment agent" includes agents directed to promoting or causing angiogenesis or angiomyogenesis.

"Carrier" includes a matrix that contains one or more treatment agents. A suitable carrier may take the form of a nanoparticle (e.g., nanosphere) or microparticle (e.g., microsphere) as the situation may dictate.

A. Treatment Agents Including a Cellular Component

Figure 1:
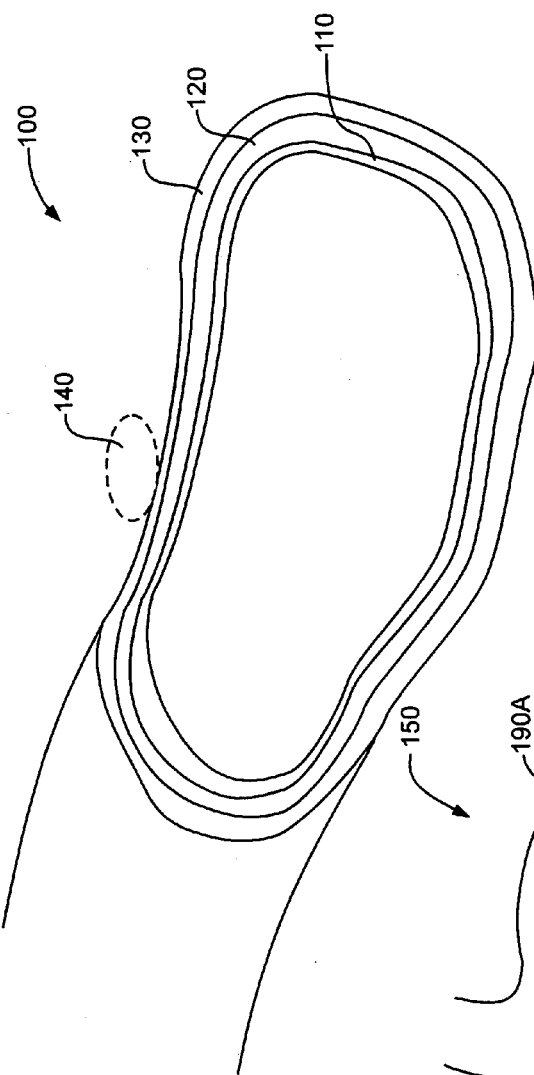
FIG. 1 schematically illustrates a perspective and cross-section view of a blood vessel.

Referring to FIG. 1, a non-diseased artery is illustrated as a representative blood vessel. Artery 100 includes an arterial wall having a number of layers. Intimal layer 10 is the innermost layer that includes the endothelium, the subendothelial layer, and the internal elastic lamina. Medial layer 120 is concentrically outward from intimal layer 110 and bounded by external elastic lamina and adventitial layer 130 is the outermost layer. There is no external elastic lamina in a vein. Medial layer 120 (in either an artery or vein) primarily consists of smooth muscle fibers and collagen. Beyond medial layer 120 and adventitial layer 130 lies the extravascular tissue including, adjacent adventitial layer 130 (and possibly including a portion of adventitial layer 130), area 140 referred to as peri-adventitial site (space) or area. Areas radially outward from a peri-adventitial space include connective tissue such as adipose tissue that is most likely located, in terms of areas around the heart, toward the epicardial surface of the heart and myocardial tissue composed of muscle fibers.

Figure 2:
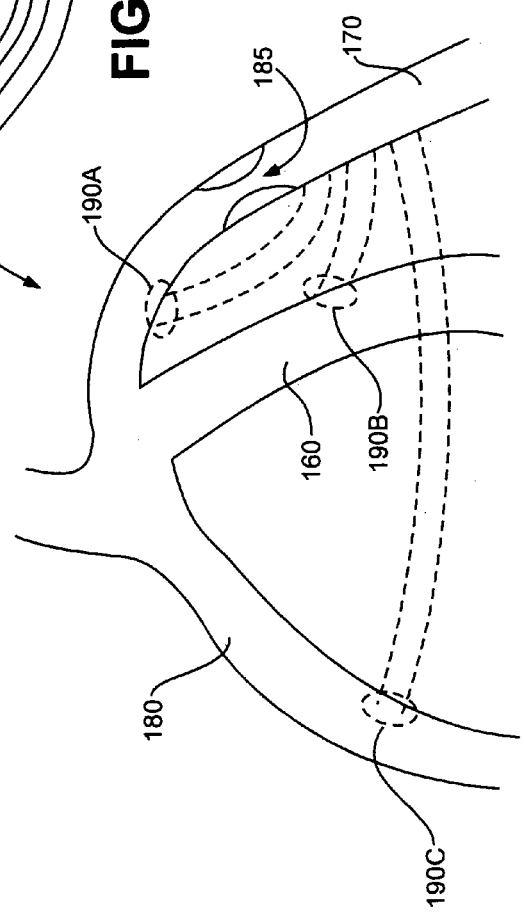
FIG. 2 schematically illustrates a planar cross-sectional view of components of a coronary artery network.

FIG. 2 illustrates components of a coronary artery network. In this simplified example, vasculature 150 includes left anterior descending artery (LAD) 160, left circumflex artery (LCX) 170 and right coronary artery (RCA) 180. Sites 190A, 190B, and 190C are preferably in the peri-adventitial space or radially outward from the peri-adventitial space (e.g., in adipose or myocardial tissue). Occlusion 185 is shown in LCX 170. Occlusion 185 limits the amount of oxygenated blood flow through LCX 170 to the myocardium that it supplied, resulting in ischemia of this tissue.

To improve the function of the artery network, it is generally desired to either remove occlusion 185 (for example through an angioplasty procedure), bypass occlusion 185 or induce therapeutic angiogenesis to makeup for the constriction and provide blood flow to the ischemic region (e.g., downstream of occlusion 185). FIG. 2 shows therapeutic angiogenesis induced at sites 190A (associated with LCX 170); 190B (associated with LAD 160); and 190C (associated with RCA 180). By inducing therapeutic angiogenesis at sites 190A, 190B, and 190C, permanent revascularization of the network is accomplished, thus compensating for reduced flow through LCX 170. The following paragraphs describe compositions, techniques and an apparatus suitable for inducing therapeutic angiogenesis.

In one embodiment, therapeutic angiogenesis is induced and modulated by locally delivering a treatment agent including a cellular component. The treatment agent may be strategically placed, for example, along an occlusion to produce an angiogenic concentration gradient to encourage the specific directional growth or expansion of collateral vessels. For example, in reference to FIG. 2, treatment agents placed at site 190A, above (as viewed) occluded vessel LCX 170 are selected such that, while up-stream, a therapeutic angiogenic or arteriogenic response will encourage growth of collaterals around occlusion 185 meeting up with LCX 170 downstream of the occlusion. Similarly, a treatment agent strategically placed at a location in a region near to LAD 160 (e.g., site 190B) will encourage bridging of collateral vessels, in this case, between LAD 160 and LCX 170. Similar encouragement and bridging may be obtained by strategically placing a treatment agent at a region of RCA 180 (such as site 190C). While the application of therapeutic angiogenesis to alleviating ischemia resulting from a flow limiting obstruction in the LCX is described, those familiar with the art will appreciate that the method described is applicable to the treatment of flow limiting obstructions in other coronary vessels and in the peripheral vasculature.

Figure 3:
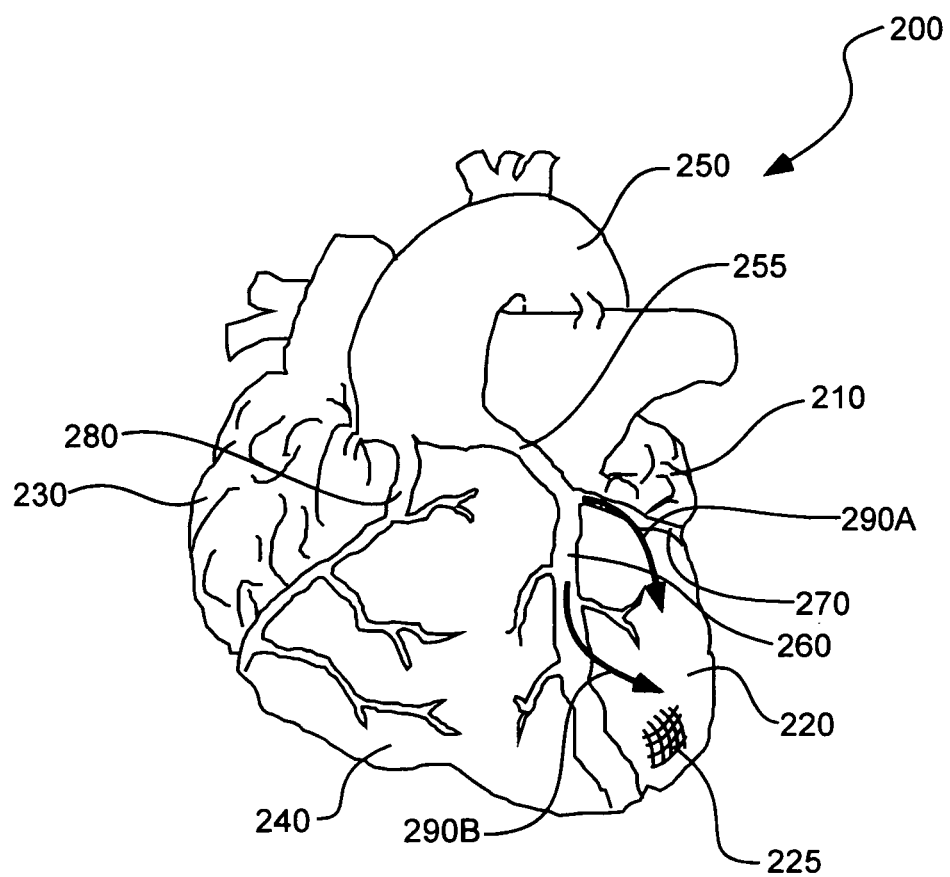
FIG. 3 is a schematic, perspective side view of a heart illustrating damage to the left ventricle.

FIG. 3 shows a schematic view of a portion of a human heart. Representatively, heart 200 includes left atrium 210, left ventricle 220, right atrium 230, and right ventricle 240. In this illustration, various arteries are shown. Included in FIG. 3 are aorta 250, left anterior descending artery (LAD) 260, left circumflex artery (LCX) 270 and right coronary artery (RCA) 280. Site 225, in this embodiment, has been damaged by an MI due to, for example, a lack of blood supply due to a partial closure or closure of LAD 160 or LCX 270 or both. The damage is representatively illustrated at the base of left ventricle 220. Representatively, the damage includes thinning of the muscle tissue of left ventricle 220.

To improve the function of left ventricle 220, therapeutic angiomyogenesis may be induced at myocardial tissue sites 290A and/or 290B. In one embodiment, therapeutic angiomyogenesis is induced by the introduction of a treatment agent including a cellular component through a percutaneous route, such as advancing a catheter into LAD 260 or LCX 270 and delivering a treatment agent beyond the blood vessel into the tissue (e.g., into or onto the adipose or myocardial tissue of left ventricle 220).

In one embodiment, a cellular component for use as or as part of a treatment agent includes adult or embyonically-derived stem cells. For example, adult-derived bone marrow cells delivered to ischemic tissue can induce an angiogenic response. Other adult stem cells including, but are not limited to, mesenchymal stem cells (MSC), multipotent adult progenator cells (MAPC), and endothelial progenator cells (EPC) may be suitable to induce angiomyogenesis. In another embodiment, suitable cells may be transfected with appropriate gene vectors to become more angiogenic or angiomyogenic and/or to improve the cells survival or preservation in the target medium (e.g., an anti-apoptosis and/or an anti-necrosis factor). In another embodiment, suitable cells may serve as homing agents that tend to attract exogenous cells. Representatively, suitable cells may be transfected with appropriate gene vectors that may function as homing factors. Suitable gene vectors that may serve one or more of the noted functions include, but are not limited to, HIF1alpha, HIF2alpha, SDF-1, IGF, TNF, IL1, PR39, and HGF.

Cellular components, such as the cells noted above, typically have receptors for particular peptide sequences (e.g., cell adhesion ligands) that allow the cellular components to adhere to collagen or other tissue that have receptors. A specific peptide receptor or binding sequence is an arginine-glycine-aspartic acid (RGD) polypeptide. Such receptor allows the cellular components to be delivered in the peri-adventitial space or beyond and be retained in the target tissue to induce or promote angiogenesis and/or angiomyogenesis for collateral formation in the heart as well as in peripheral circulation, such as for applications involving stroke, peripheral arterial disease (PAD), etc.

In one embodiment, the treatment agent including a cellular component may be delivered percutaneously, such as through catheter/needle delivery. Suitable delivery mechanisms include delivery of a treatment agent including an isotonic saline solution of cells, such as stem cells. Alternatively, the cells or cellular components may be encapsulated in matrices/gels that may improve the engraftment of the cells in the target zone. Suitable encapsulation matrices or gels may further allow the delivered treatment agent to become allogenic. In another embodiment, matrices or gels may include beneficial factors, such as homing factors or anti-apoptosis factors, so that when cells are delivered in these matrices or gels, the matrices or gels have the beneficial factors dispersed therein, for example, as a protein (e.g., SDF-1) or peptide (e.g., PR11, PR39). Beneficial factors dispersed in matrices or gels of a treatment agent may be as an alternative to transfecting such factors into a cell of the treatment agent or in addition to transfecting such factors into a cell of the treatment agent.

One way to form a treatment agent including a cellular component in a matrix or gel includes an alginate-derived hydrogel. Alginates are composed of (1-4)-linked β-D-mannuronic acid (M units) and α-L-guluronic acid (G units) monomers which vary along a polymer chain depending on the source of the alginate. The alginate molecule of a block copolymer is composed of regions of sequential M units, regions of sequential G units, and regions of atactically organized M and G units. Divalent cations like calcium ($Ca^{2+}$)

cooperatively bind between the G units of adjacent alginate chains, creating ionic interchain bridges that cause gelling of aqueous alginate solutions.

In one embodiment of forming a alginate hydrogel treatment agent including a cellular component, suitable cells (e.g., stem cells) may be added to a solution of sodium alginate and isotonic saline with optional additional ions (e.g., magnesium, potassium) prior to injection. The alginate may be covalently modified with a cell adhesion ligand such as RGD, GRTY (where Y is tyrosine), etc., containing peptides via a carbodiimide coupling to improve or enhance cell attachment to the alginate. A suitable covalent modification with a peptide sequence is described in "Alginate Hydrogels as Synthetic Extracellular Matrix Materials," Rowley, et al., Biomaterials 20 (1999), 45-53. In another embodiment, the alginate may be covalently modified with (e.g., covalently conjugated to) a gelatin or collagen (e.g., a gelatin or collagen commercially available from FibroGen, Inc. of South San Francisco, Calif.). The alginate solution including the cellular component may be injected through one needle of a catheter while a calcium chloride ($CaCl_2$) solution is injected through a second catheter needle. Alternatively, the alginate solution including the cellular component and a calcium ion solution may be introduced in series through a single needle. The calcium ions will cross-linked with the alginate and form a gel in situ.

Another technique for forming a matrix or gel treatment agent including a cellular component includes forming discrete particles (e.g., microspheres) of a hydrogel such as an alginate hydrogel. Representatively, a cellular component may be added to a solution of sodium alginate or modified sodium alginate as described above. The solution is placed into a spray gun or an atomizer such as commercially available from Efd-inc of East Providence, R.I. A solution of alginate-covered cells may be sprayed into an agitated solution of calcium chloride. The atomized alginate-covered cells form discrete particles (e.g., microspheres) on exiting the atomizer. When these particles enter the calcium solution, the alginate portion is gelled and becomes generally insoluble in water. The particles may then be separated by centrifugation or filtration, washed, and resuspended in an ionic solution such as HYPOTHERMOSOL™, commercially available from BioLife Solutions, Inc. of Binghamton, N.Y. The particles can then be injected through a single needle catheter. In either this technique or the in situ formed alginate hydrogel described above, the alginate provides a porous network for the passage of nutrients and minerals. Attached peptide sequences (e.g., RGD) provide adhesion of the hydrogel to collagen or other tissue at the treatment site.

Another technique for introducing a treatment agent including a cellular component at a treatment site that may form a matrix or gel is through the use of ionic polymers. Representatively, cells, such as stem cells, can be mixed with an anionic polymer (e.g., a solution of poly(styrene) sulfonate (PSS) or PSS in phosphate buffered saline (PBS)). The solution may be injected through a needle catheter of a dual needle catheter system. A cationic polymer such as diethylaminoethyl dextran (DEAE dextran) or ethoxylated polyethylenimine (ethoxylated PEI) may be injected through the other needle. Alternatively, the polymer including the treatment agent and the cationic polymer may be introduced in series through a single needle. The mixture of the anionic and cationic polymers form a gel in situ that will encapsulate the cells and retain the cells at a treatment site.

In another embodiment, a treatment agent including a cellular component may be introduced at a treatment site with a gelatin or collagen. A suitable genetically engineered collagen may include a peptide sequence (e.g., an RGD sequence) for attachment of the collagen at the treatment site. One suitable collagen is commercially available from FibroGen, Inc. of South San Francisco, Calif. Representatively, a treatment agent including a cellular component may be delivered with the collagen through a single needle catheter or a dual needle catheter system.

A further technique for introducing a treatment agent including a cellular component is through the formation of porous microspheres. Representatively, porous gelatin microspheres may be formed such as described in "Accelerated Tissue Generation Through Incorporation of Basic Fiberglass Groove Factor-Impregnated Gelatin Microspheres into Aritificial Dermous," Kawai et al., Biomaterials 21, (2000), 489-499. The porous gelatin microspheres described in Kawai may be modified by using a water soluble porogen (e.g., polyethylene glycol, sugar, etc.) in the initial water in oil emulsion. The spheres are allowed to cross-link with glutoraldehyde or geneprin, then the porogen can be dissolved by soaking in water to yield porous particles (e.g., microspheres). The porous particles may be seeded with a treatment agent including suitable cells (e.g., stem cells) by dropping an aqueous solution of the treatment agent into the particles. The cells will attach to the particles. The cell-attached particles may be introduced to a treatment site through a single needle catheter.

In the above embodiments, a composition is described including a treatment agent including a cellular component. Examples include, but are not limited to, the composition in the form of a solution (e.g., isotonic saline) or gelled particles in solution that may be introduced, representatively, through a single needle of a needle catheter assembly. In other examples, compositions intended to be introduced (perhaps with multiple injections or needles) in the form of a matrix or gel are described. In another embodiment, the composition or multiple components (compositions) that comprise the composition may be prepared in the form of a kit suitable in one embodiment for inducing and/or modulating therapeutic angiogenesis or therapeutic angiomyogenesis. The kit may contain desired doses or loadings of the treatment agent and/or the precursors to form the matrix or gel.

B. Catheter Assembly

In another embodiment, an apparatus (a catheter assembly) is described for accurately locating a treatment agent at a location in a blood vessel (preferably beyond the media layer) or in a peri-adventitial space adjacent to a blood vessel, or areas radially outward from a peri-adventitial space including at tissue locations such as the tissue of the myocardium. It is appreciated that a catheter assembly is one technique for introducing treatment agents and the following description is not intended to limit the application or placement of the treatment agent compositions described above.

Referring now to the drawings, wherein similar parts are identified by like reference numerals, FIGS. 4-7 illustrate one embodiment of a delivery apparatus. In general, the delivery apparatus provides a system for delivering a substance, such as a treatment agent or a combination of treatment agents optionally presented as a sustained release composition, to or through a desired area of a blood vessel (a physiological lumen) or tissue in order to treat a localized area of the blood vessel or to treat a localized area of tissue possibly located adjacent to the blood vessel. The delivery apparatus is similar in certain respects to the delivery apparatus described in commonly-owned, U.S. patent application Ser. No. 09/746,498 (filed Dec. 21, 2000), titled "Local Drug Delivery Catheter with Retractable Needle," of Steward et al.; U.S. patent application Ser. No. 10/394,834 (filed Mar. 20, 2003), titled "Drug Delivery Catheter with Retractable Needle," of Chow et al.; and U.S. patent application Ser. No. 10/749,354 (filed Dec. 31, 2003), titled "Needle Catheter." of Chan, et al. Each of these applications is incorporated herein by reference. The delivery apparatus described is suitable, in one embodiment, for a percutaneous delivery of a treatment agent where a desired form of the treatment agent is introduced through a single catheter needle or is introduced through multiple needles and formed, for example, in situ.

Figure 4:
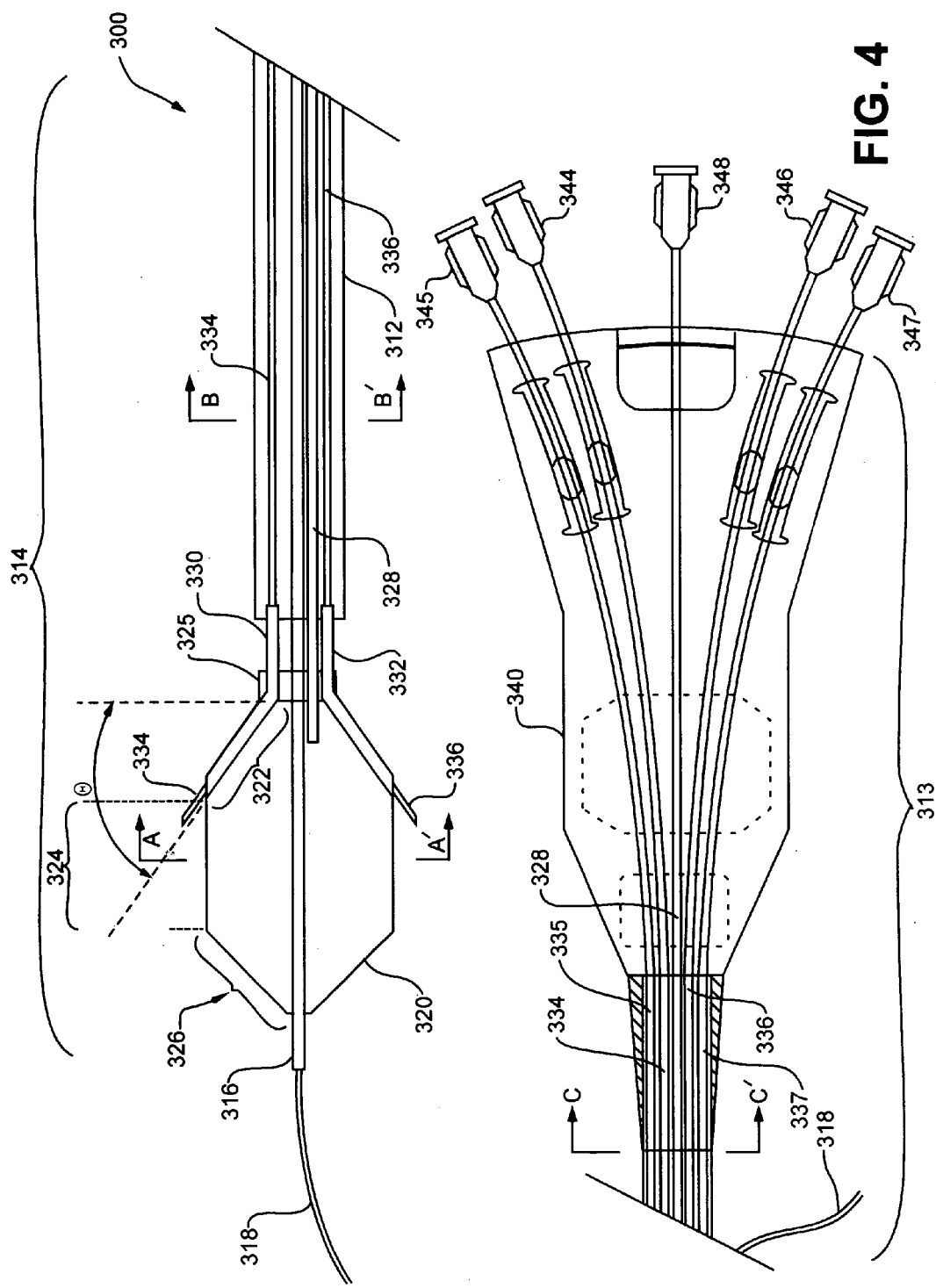
FIG. 4 is a simplified cross-sectional view of an embodiment of a substance delivery apparatus in the form of a catheter assembly having a balloon and a therapeutic substance delivery assembly.

Referring to FIG. 4, the delivery apparatus includes a catheter assembly 300, which is intended to broadly include any medical device designed for insertion into a blood vessel or physiological lumen to permit injection and/or withdrawal of fluids, to maintain the potency of the lumen, or for any other purpose. In one embodiment, catheter assembly 300 is defined by elongated catheter body (cannula) 312 having proximal portion 313 and distal portion 314.

Referring to FIG. 4, catheter assembly 300 includes catheter body 312 extending from proximal portion 313 to distal portion 314. In this example, guidewire cannula 316 is formed within catheter body 312 for allowing catheter assembly 300 to be fed and maneuvered over a guidewire (guidewire 318 shown at this point within a lumen of guidewire cannula 316). Guidewire cannular extends, in this embodiment, from proximal portion 313 to distal portion 314, thus describing an over the wire (OTW) assembly. In another embodiment, typically described as a rapid exchange (RX) type catheter assembly, guidewire cannula 316 extends only through a portion of catheter body 312, for example, beginning and ending within distal portion 314. It is appreciated that guidewire 318 may be retracted or removed once catheter assembly 300 is placed at a region of interest, for example, within a blood vessel (e.g., artery or vein).

In the embodiment of FIG. 4, catheter assembly 300 includes balloon 320 incorporated at distal portion 314 of catheter assembly 300. Balloon 320 is an expandable body in fluid communication with inflation cannula 328 disposed within catheter body 312. Inflation cannula 328 extends from balloon 320 within distal portion 314 through inflation port 348 at proximal portion 313 (e.g., at a proximal end of catheter assembly 300).

In the embodiment shown in FIG. 4, balloon 320 is in an expanded or inflated state. Balloon 320 is selectively inflatable to dilate from a collapsed configuration to a desired or controlled expanded configuration. Balloon 320 can be selectively inflated by supplying a fluid (e.g., liquid) into a lumen of inflation cannula 328 at a predetermined rate of pressure through inflation port 348. Likewise, balloon 320 is selectively deflatable to return to a collapsed configuration or deflated profile.

In one embodiment, balloon 320 can be defined by three portions: distal taper wall 326, medial working length 324, and proximal taper wall 322. In one embodiment, proximal taper wall 322 can taper at any suitable angle θ, typically between about 15° to less than about 90°, when balloon 320 is in an expanded (inflated) configuration.

Balloon 320 can be made from many suitable material, including, but not limited to, polymers and copolymers of polyolefins, polyamides, polyester and the like. The specific material employed should be compatible with inflation or expansion fluid and must be able to tolerate the pressures that are developed within balloon 320. One suitable material is an elastomeric nylon such as PEBAX™, a condensation polymerized polyether block polyamide. PEBAX™ is a trademark of ATOCHEM Corporation of Puteaux, France. Other suitable materials for balloon 320 include, but are not limited to, a biocompatible blend of polyurethane and silicone, or a styrenic block copolymer (SBC) or blend of SBCs. Distal taper wall 326, medial working length 324, and proximal taper wall 322 can be bound together by seams or be made out of a single seamless material. A wall of balloon 320 (e.g., at any of distal taper wall 326, medial working length 324 and/or proximal taper wall 322) can have any suitable thickness so long as the thickness does not compromise properties that are critical for achieving optimum performance. Relevant properties include, but are not limited to, high burst strength, low compliance, good flexibility, high resistance to fatigue, the ability to fold, the ability to cross and recross a desired region of interest or an occluded region in a physiological lumen and low susceptibility to defects caused by handling. By way of example, not limitation, a suitable thickness of a balloon wall can be in the range of about 0.0005 inches to 0.002 inches, the specific specifications depending on the procedure for which balloon 320 is to be used and the anatomy and size of the target lumen in which balloon 320 is to be inserted.

Balloon 320 may be inflated by the introduction of a fluid (e.g., liquid) into inflation cannula 328 (through inflation port 348 at a point outside a physiological lumen). Liquids containing therapeutic and/or diagnostic agents may be used to inflate balloon 320. In one embodiment, balloon 320 may be made of a material that is permeable to such therapeutic and/or diagnostic agents. To inflate balloon 320, a suitable fluid may be supplied into inflation cannula 328 at a predetermined pressure, for example, between about 1 and 20 atmospheres (atm). A specific pressure depends on various factors, such as the thickness of the balloon wall, the material of which balloon 320 is made, the type of substance employed, and the flow rate that is desired.

Catheter assembly 300, in the embodiment shown in FIG. 4 also includes delivery cannula 330 and delivery cannula 332 each connected to proximal taper wall 322 of balloon 320 and extending at a proximal end, in one embodiment, into a portion of catheter body 312 of catheter assembly 300. Representatively, a suitable length for delivery cannula 330 and delivery cannula 332 is on the order of three to 6.5 centimeters (cm). Delivery cannula 330 and delivery cannula 332 can be made from any suitable material, such as polymers and copolymers of polyamides, polyolefins, polyurethanes, and the like. Catheter assembly 300, in this view, also includes needle 334 and needle 336. Needle 334 and needle 336 extend from distal portion 314 to proximal portion 313 of catheter assembly 300. At distal portion 314, needle 334 is disposed through a lumen of delivery cannula 330 and needle 336 is disposed through a lumen of delivery cannula 332. Thus, a dimension of delivery cannula 330 and delivery cannula 332 are each selected to be such to allow a delivery device such as a needle to be moved therethrough. Representatively, delivery cannula 330 has an inner diameter (lumen diameter) on the order of 0.0155 inches and an outer diameter on the order of 0.0255 inches. FIG. 4 shows catheter assembly 300 with each of needle 334 and needle 336 deployed, i.e., extending from an end of delivery cannula 330 and delivery cannula 332, respectively.

Figure 5:
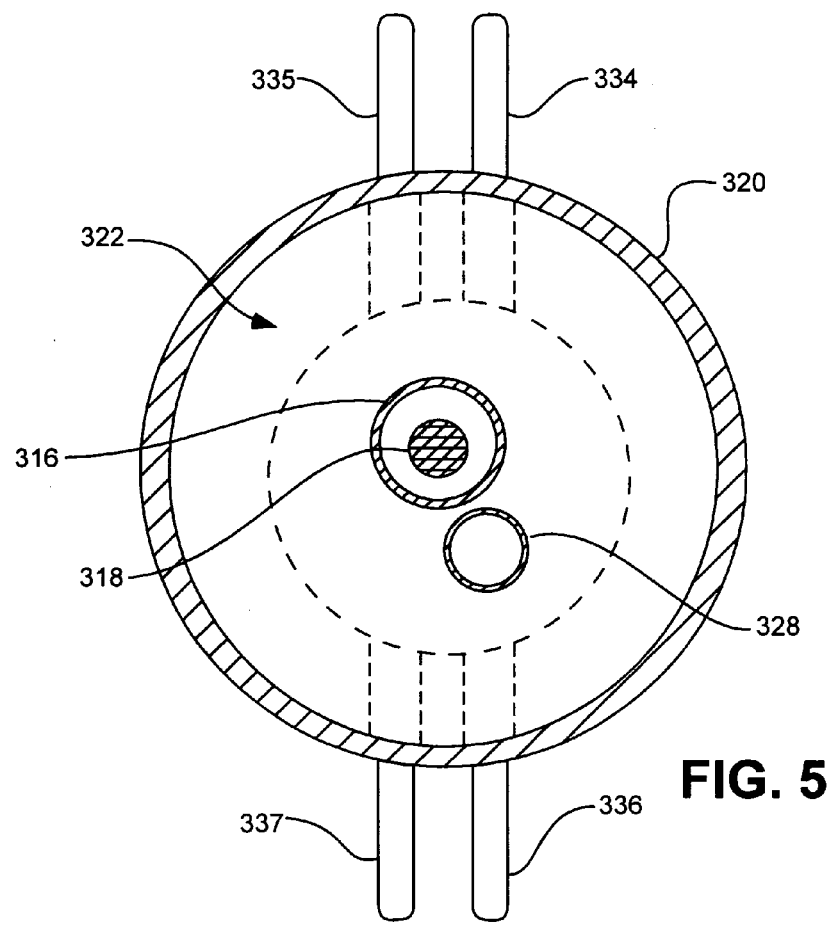
FIG. 5 schematically illustrates a planar cross-sectional view of the substance delivery apparatus of FIG. 4 through line A-A'.

FIG. 5 shows a cross-section through line A-A' of FIG. 4. From this view, catheter assembly 300 includes four needles (and four delivery cannulas). FIG. 5 shows needle 335 adjacent (e.g., in contact with or spaced a few millimeters from) needle 334 and needle 337 similarly adjacent needle 336. Representatively, delivery cannula 330 and delivery cannula 332 may be spaced either radially and/or circumferentially from each other, for example, between 45° and 180° apart. FIG. 4 and FIG. 5 shows delivery cannula 330 and needle 334 circumferentially spaced about 180° from delivery cannula 332 and needle 336. In other embodiments, a catheter assembly may include fewer needles (e.g., one needle) or more needles (e.g., greater than four). Representatively, a suitable catheter assembly may include two needles such as needle 334 and needle 335 adjacent one another. In an embodiment where a treatment agent is introduced as a two part composition to form a matrix or gel in situ, one part can be introduced through needle 334 and a second part through needle 335.

FIG. 4 shows delivery cannula 330 and delivery cannula 332 each connected to an exterior surface of balloon 320. Specifically, a distal end of each of delivery cannula 330 and delivery cannula 332 extend to a point equivalent to or less than a length of proximal taper wall 322 of balloon 320. One suitable technique for connecting delivery cannula 330 or delivery cannula 332 to balloon 320 is through an adhesive. A suitable adhesive includes a cyanocrylate (e.g., LOCTITE 414™) adhesive, particularly where the balloon material is a PEBAX™ material.

Catheter assembly 300 in the embodiment shown in FIG. 4 also includes sheath ring 325. Sheath ring 325 is positioned over, in this embodiment, guidewire cannula 316, inflation cannula 328, delivery cannula 330, and delivery cannula 332 and additional delivery cannulas for needle 335 and needle 337, respectively. In one embodiment, sheath ring 325 functions to inhibit delamination of the delivery cannulas from proximal taper wall 322 of balloon 320 and, where thermally sealed to the various cannulas may reduce the spacing (on a proximal side of sheath ring 325) of the cannulas. Thus, a distal end of sheath ring 325 is placed, in one embodiment, at a point immediately proximal to where a delivery cannula will rotate, bend or plicate in response to the expansion or inflation of balloon 320. In one embodiment, sheath ring 325 is a biocompatible material that is capable of connecting to (e.g., bonding to) a material for balloon 320 and to a material for each of the noted cannulas that it surrounds. Representatively, a body of sheath ring 325 has a length from a proximal end to a distal end on the order of 0.25 millimeters (mm) to 0.75 mm, such as 0.5 mm.

One way to form catheter assembly 300 including sheath ring 325 is to initially connect (e.g., bond) balloon 320 at a distal end to guidewire cannula 316. Balloon 320 is also connected (e.g., bonded) at a proximal end to guidewire cannula 316 and inflation cannula 328. Once balloon 320 is sealed at each end, balloon 320 is inflated. The delivery cannulas are aligned on inflated balloon 320 with a distal end at reference point corresponding to a distal end of proximal taper wall 322 of balloon 320. Distal ends of the delivery cannulas may be tapered to approximate or match a plane defined by medial working length 324 of balloon 320 when balloon 320 is in an inflated state. The delivery cannulas may then be glued or affixed to balloon 320 through an adhesive such as a cyanoacrylate adhesive. Next, sheath ring 325 is loaded (advanced proximal to distal) onto a proximal end of balloon 320 and the cannulas of catheter assembly 300 (e.g., guidewire cannula 316, inflation cannula 328, delivery cannula 330 and delivery cannula 332, and delivery cannulas for needle 335 and needle 337). A material of sheath ring 325 of a polymer such as PEBAX 40D™ may be connected to balloon 320 and the delivery cannulas by a thermal seal process. As an alternative to a thermal seal process for connecting sheath ring 325, sheath ring 325 may be connected to balloon 320 and the delivery cannulas by an adhesive, such as cyanoacrylate adhesive.

As noted above, each delivery cannula (e.g., delivery cannula 330, delivery cannula 332) plicates or bends distal to sheath ring 325 with the inflation of balloon 320. Thus, the path to be traveled by each needle (e.g., needle 334, needle 335, needle 336, and needle 337) includes this bend or plication. To facilitate a travel through a bend or plication region in each delivery cannula and to inhibit puncturing of the respective delivery cannula, each delivery cannula may include a deflector disposed along an interior wall. Representatively, a suitable deflector includes a ribbon of thin, generally flexible and generally resilient material (e.g., thickness on the order of about 0.0005 inches to about 0.003 inches and width on the order of about 0.005 inches and 0.015 inches). Suitable deflector materials, dimensions and connections within a catheter assembly are described in commonly-owned, U.S. patent application Ser. No. 09/746,498 (filed Dec. 21, 2000), titled "Local Drug Delivery Catheter with Retractable Needle," of Steward et al.; U.S. patent application Ser. No. 10/394,834 (filed Mar. 20, 2003), titled "Drug Delivery Catheter with Retractable Needle," of Chow et al.; and U.S. patent application Ser. No. 10/749,354 (filed Dec. 31, 2003), titled "Needle Catheter." of Chan, et al.

Figures 6, 7:
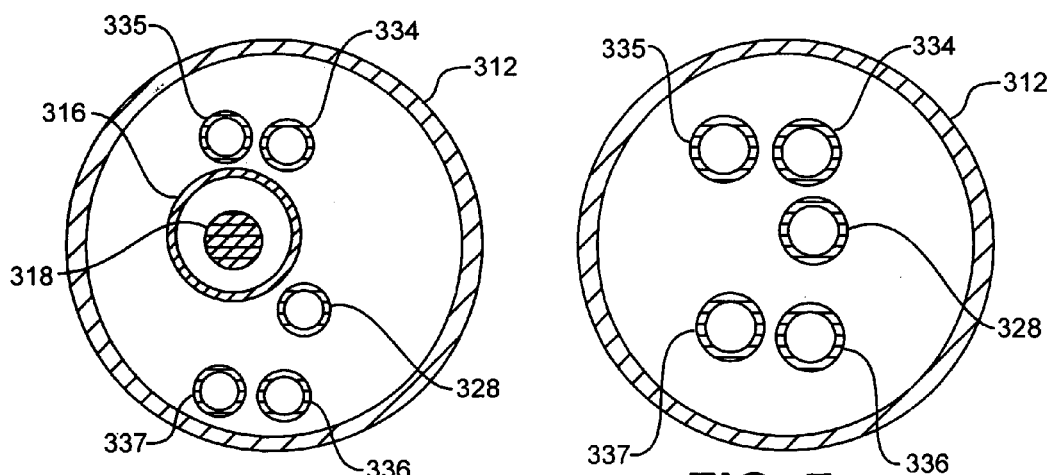
FIG. 6 schematically illustrates a planar cross-sectional view of the substance delivery apparatus of FIG. 4 through line B-B'.
FIG. 7 schematically illustrates a cross-sectional view of the distal section of the substance delivery apparatus of FIG. 4 through line C-C'.

FIG. 6 shows a cross-section through line B-B' of FIG. 4. FIG. 6 shows catheter body 312 as a cannula including a lumen therethrough. Inside the lumen of catheter body 312 is needle 334, needle 335, needle 336, and needle 337. Also disposed in a lumen of catheter body 312 is inflation cannula 328 and guidewire cannula 316. Disposed within a lumen of guidewire cannula 316 is guidewire 318.

FIG. 7 shows a cross-section through line C-C' of FIG. 4, illustrating a cross-section through proximal portion 313 of catheter assembly 300. FIG. 7 shows catheter body 312 having a lumen therethrough. Disposed within the lumen of catheter body 312 is needle 334, needle 335, needle 336 and needle 337. A lumen of catheter body 312, at this cross-section, also includes inflation cannula 328. Guidewire cannula 316, in this one embodiment, does not extend proximally as far as line C-C'. It is appreciated that the cross-sectional area of catheter body 312 may be minimized (minimum profile) at proximal portion 313 of catheter assembly 300 because fewer articles are accommodated in a lumen of catheter body 312 (e.g., at this point guidewire cannula 316 is not present).

Referring again to FIG. 4, proximal portion 313 of catheter assembly 300 is intended, in one embodiment, to reside outside a patient while the remainder of catheter assembly 300 is percutaneously introduced into, for example, the cardiovascular system of a patient via the brachial or femoral artery. In this embodiment, proximal portion 313 of catheter assembly 300 includes hub 340. Hub 340 includes needle 334, needle 335, needle 336, needle 337, and inflation cannula 328. In one embodiment, relative to the materials for the various cannulas described, a housing of hub 340 is a hard or rigid polymer material, e.g., a polycarbonate or acrylonitrile bubadiene styrene (ABS). A distal end of hub 340 has an opening to accommodate a proximal end of catheter body 312. Hub 340 also has a number of cavities at least partially therethrough (extending in a distal to proximal direction) to accommodate needle 334, needle 335, needle 336, needle 337, and inflation cannula 328. A proximal portion of hub 340 flares to separate a spacing between the needles, and inflation cannula 328.

FIG. 4 shows a proximal end of needle 334, needle 335, needle 336, and needle 337 each connected (e.g., through an adhesive) to respective injection port 344, injection port 345, injection port 346, and injection port 347. In one embodiment, each injection port includes a luer fitting for conventional syringe attachment. Each injection port allows for the introduction of a treatment agent, including but not limited to a drug or cellular component (e.g., stem cell) or a material (e.g., precursor) to form a matrix or gel with a treatment agent. In this embodiment, inflation cannula 328 terminates at the distal end of balloon inflation port 348.

In one embodiment, one or more needles (needle 334, needle 335, needle 336, needle 337) may be used to deliver a treatment agent to a treatment site. For example, a single needle may be used to introduce a treatment agent including a cellular component to be introduced, for example, in an isotonic saline solution and/or as a solution of gel microspheres. Alternatively, adjacent needles, such as needle 334 and needle 335, may be used to deliver a treatment agent (e.g., a treatment agent including a cellular component and a first matrix or gel precursor and a second matrix or gel precursor (e.g., a non-therapeutic angiogenic or angiomyogenic substance), respectively.

In one embodiment, catheter assembly 300 also includes or can be configured to include an imaging assembly. Suitable imaging assemblies include ultrasonic imaging assemblies, optical imaging assemblies, such as an optical coherence tomography (OCT) assembly, magnetic resonance imaging (MRI). One embodiment of catheter assembly 300 illustrated in FIG. 4 may include an OCT imaging assembly.

Figure 8:
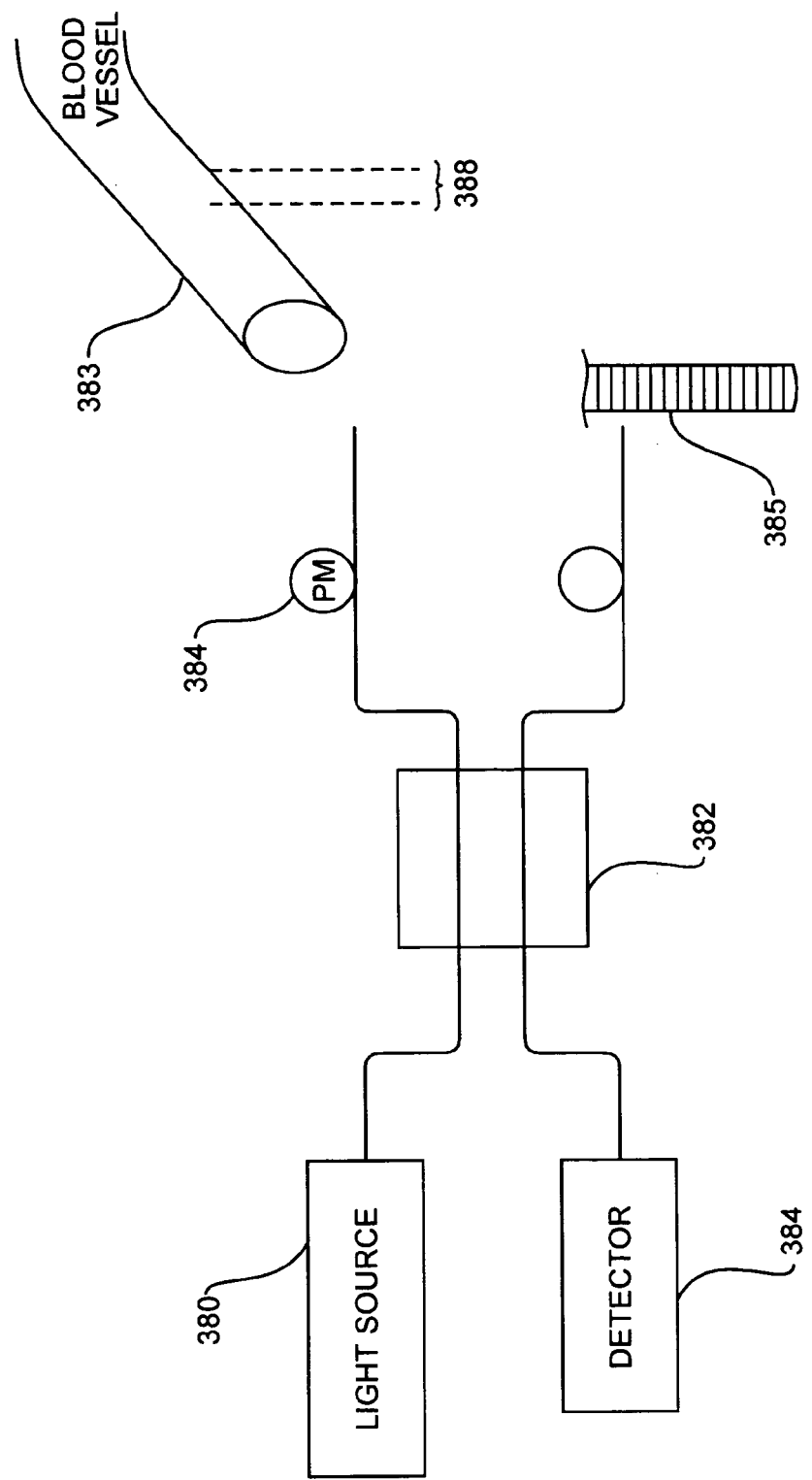
FIG. 8 schematically illustrates an optical imaging system for use in a substance delivery apparatus such as a catheter assembly.

OCT uses short coherence length light (typically with a coherent length of about 10 to 100 microns) to illuminate the object (e.g., blood vessel or blood vessel walls). Light reflected from a region of interest within the object is combined with a coherent reference beam. Interference occurs between the two beams only when the reference beam and reflective beam have traveled the same distance. FIG. 8 shows one suitable OCT setup similar in some respects to ones disclosed in U.S. Pat. Nos. 5,465,147; 5,459,570; 5,321,501; 5,291,267; 5,365,325; and 5,202,745. A suitable optical assembly for use in conjunction with a catheter assembly is made with fiber optic components that, in one embodiment, can be passed through the guidewire lumen (e.g., guidewire cannula 316 of FIG. 4). Light having a relatively short coherence length, $l_c$ (given by $l_c=C/\Delta f$, where $\Delta f$ is the spectral bandwidth) is produced by light source 380 (e.g., incandescent source, laser source or light emitting diode of suitable wavelength) and travels through 50/50 coupler 382 where it is divided into two paths. One path goes to blood vessel 383 to be analyzed and the other path goes to a moveable reference mirror 385. The probe beam reflected from blood vessel 383 and the reference beam reflected from reference mirror 385 are combined at coupler 382 and sent to detector 387. The optical path traversed by the reflected probe beam and the reference beam are matched to within one coherence length such that coherent interference can occur upon recombination at coupler 382.

Phase modulator 384 produces a temporal interference pattern (beats) when recombined with the reference beam. Detector 387 measures the amplitude of the beats. The amplitude of the detected interference signal is the measure of the amount of light scattered from within a coherence gate interval 388 inside, in this case, blood vessel 383 that provides equal path lengths for the probe and reference beams. Interference is produced only for light scattered from blood vessel 383 which has traveled the same distance as light reflected from reference mirror 385.

In one embodiment, the optical fiber portion of the OCT imaging system can be inserted in a lumen of a guidewire cannula of an over the wire catheter with the guidewire lumen terminating at the imaging wire coupling. The body of the guidewire cannula (e.g., guidewire cannula 316 of catheter assembly 300 of FIG. 4) and the body of the balloon assembly (e.g., balloon 320 in FIG. 4) should be transparent at the distal end to allow optical imaging (e.g., through the body of balloon 320). Thus, once the catheter assembly is placed, at a desired location within, for example, a blood vessel, guidewire 318 may be removed and replaced with an optical fiber. In a catheter assembly such as illustrated in FIG. 4, the replacement of the guidewire with an optical fiber is done, in one embodiment, at low inflation pressure of balloon 320.

Where an optical fiber is substituted for a guidewire, the dimensions of a catheter does not have to be modified. Optical fibers having an outer diameter of 0.014, 0.018, or 0.032 inches (0.36, 0.46, or 0.81 mm, respectively) are suitable for current guidewire lumens. Other imaging components (e.g., fiber rotator, imaging screen, OCT system components, etc.) may be connected to the optical fiber as it extends out proximal portion of the catheter assembly 300 (see FIG. 4). Such components include, but are not limited to, a drive coupling that provides rotation and forward/reverse movement of the optical fiber; a detector, and an imaging screen.

Figure 9:
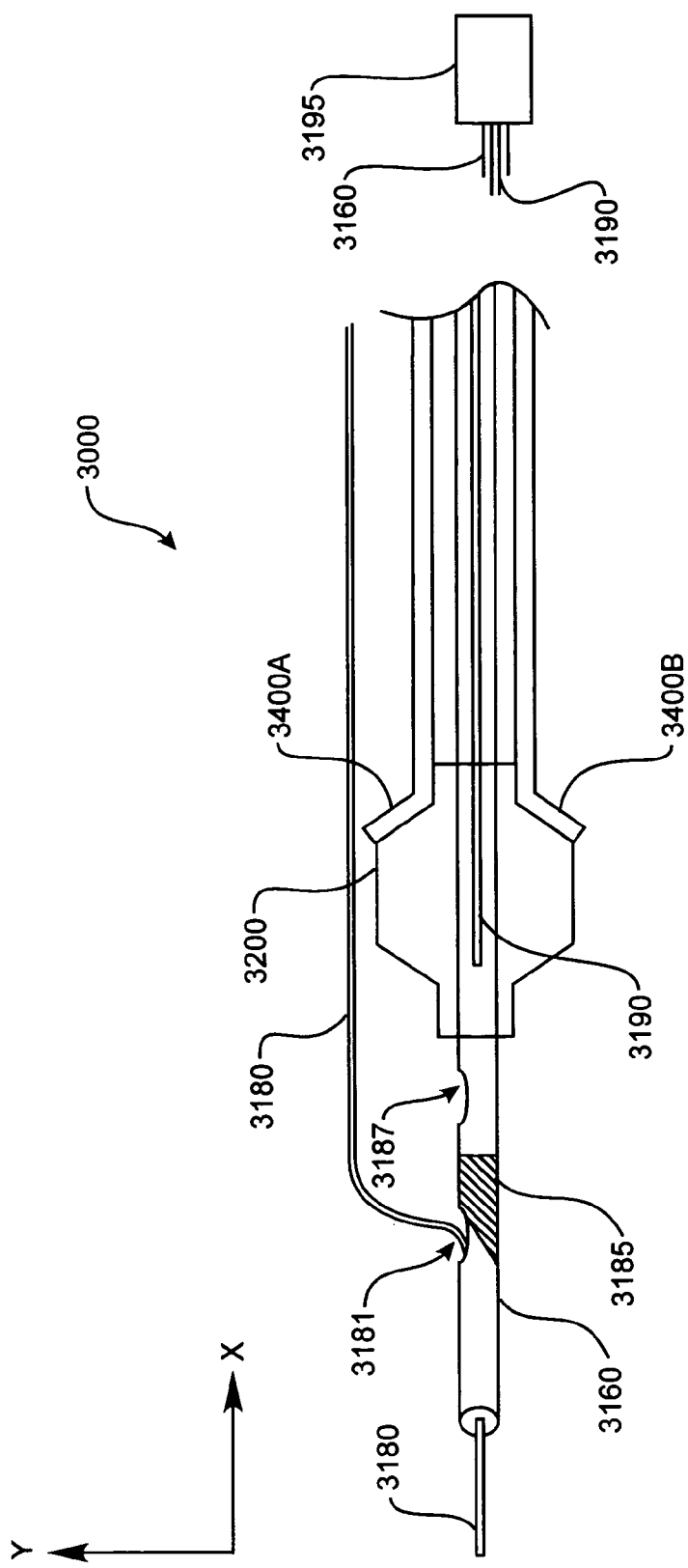
FIG. 9 schematically illustrates a cross-sectional side view of components of an alternative catheter assembly including an optical imaging system.

FIG. 9 shows another embodiment of a catheter assembly including an OCT apparatus. In this embodiment, guidewire 3180 and optical fiber 3190 "share" common imaging lumen or cannula 3160. Cannula 3160 is preferably made of a transparent material at the distal end utilized by optical fiber 3190. Catheter assembly 3000 also includes balloon 3200 with needle cannulas 3400A and 3400B (and possibly more or less) connected to a proximal portion of balloon 3200.

Referring to FIG. 9, cannula 3160 is mounted on guidewire 3180 at distal tip 3181 (i.e., distal to balloon 3200). Guidewire 3180 and optical fiber 3190 are separated in cannula 3160 by plug 3185 of, for example, a polymer or copolymer material, having dimensions suitable to fill the lumen. Suitable polymers include polyimides, polyurethanes, and polyolefins. A portion of plug 3185 may also serve as a ramp for the guidewire port. In this embodiment, imaging of a blood vessel (e.g., imaging of a wall of a blood vessel for thickness determination) is accomplished from a portion of cannula 3160 corresponding with the location of balloon 3200. Thus, balloon 3200 is also preferably made of a transparent material. Flush port 3187 may also be included for clearing imaging portion of cannula 3160.

At a proximal end, cannula 3160 of the embodiment illustrated in FIG. 9 terminates in drive coupling 3195. Drive coupling 3195 provides rotation and forward/reverse direction movement of optical fiber 3190 and connection to the OCT system.

In another embodiment, the imaging assembly is based on ultrasonic technology. Ultrasonic systems are referenced in U.S. Pat. Nos. 4,794,931; 5,100,185; 5,049,130; 5,485,486; 5,827,313; and 5,957,941. In one example, an ultrasonic imaging assembly, representatively including an ultrasonic transducer, may be exchanged for a guidewire through a lumen of a guidewire cannula such as described above with reference to the first OCT embodiment. In another embodiment, a guidewire and ultrasonic transducer "share" a common lumen of an imaging cannula similar to the embodiment described with reference to FIG. 9 and the accompanying text. In either example, imaging of, for example, a blood vessel will take place through the balloon. In the case of ultrasonic imaging, the balloon and guidewire cannula need not be transparent.

Figure 10:
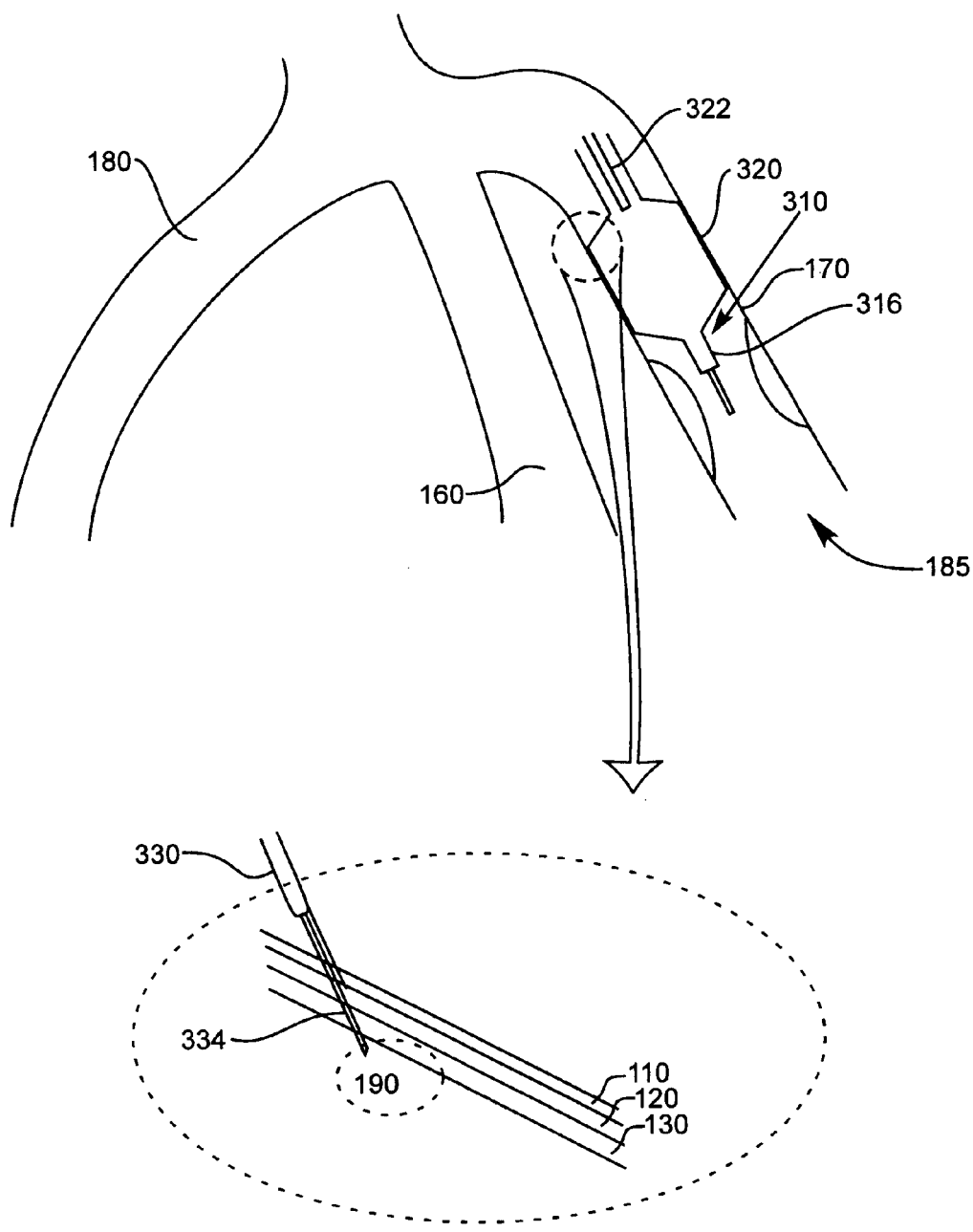
FIG. 10 schematically illustrates the portion of coronary artery network of FIG. 2 having a catheter assembly introduced therein.
Figure 11:
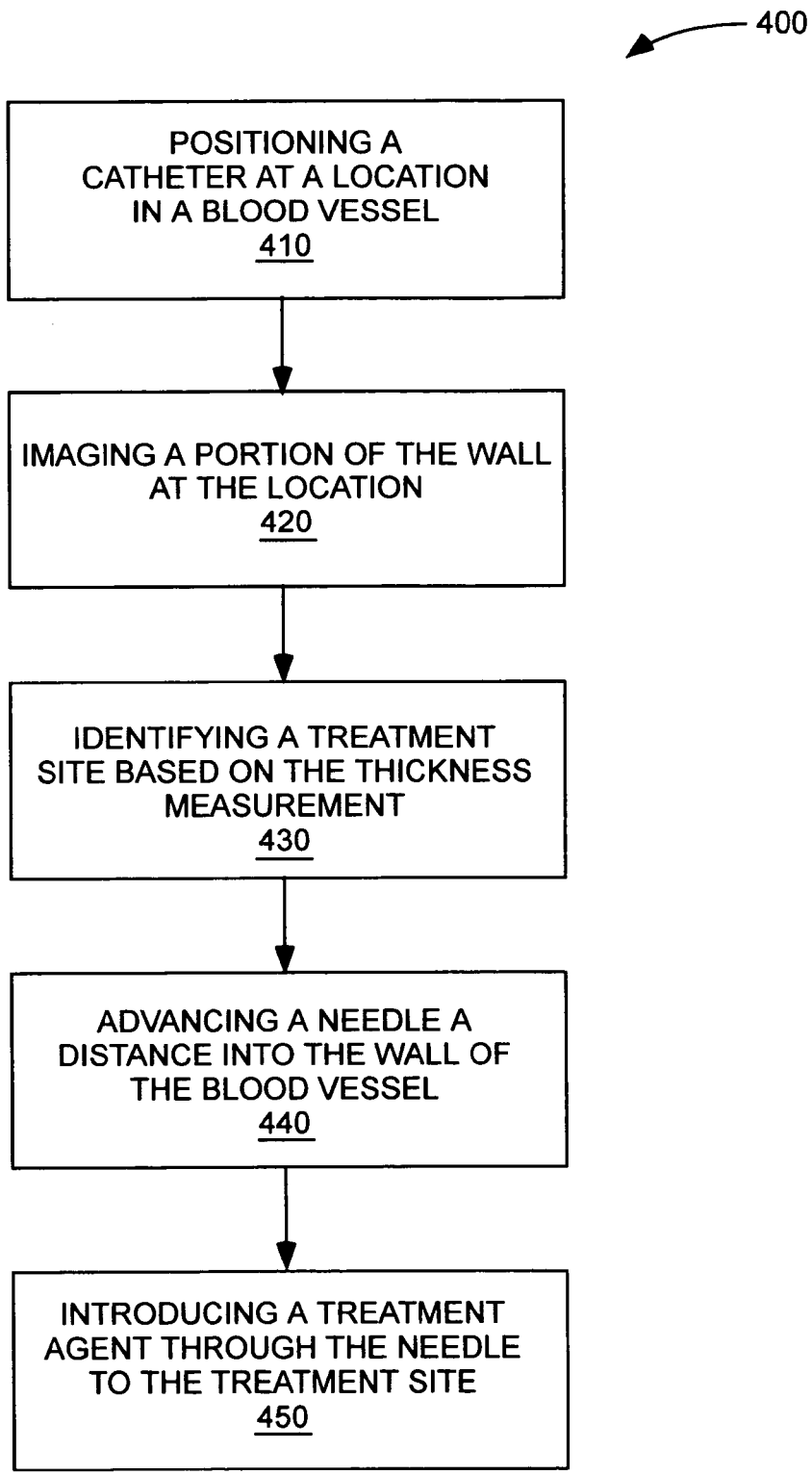
FIG. 11 presents a block diagram for introducing a treatment agent.

The catheter assembly described with reference to FIG. 4 or FIG. 9 may be used to introduce a treatment agent such as described above at a desired location. FIG. 10 illustrates one technique. FIG. 11 presents a block diagram of one technique. With reference to FIGS. 10 and 11 and catheter assembly 300 of FIG. 4, in a one procedure, guidewire 318 is introduced into, for example, an arterial system of the patient (e.g., through the femoral artery) until the distal end of guidewire 318 is upstream of the narrowed lumen of the blood vessel (e.g., upstream of occlusion 185). Catheter assembly 300 is mounted on the proximal end of guidewire 318 and advanced over the guidewire 318 until catheter assembly 300 is position as desired. In the example shown in FIG. 10, catheter assembly 300 is positioned so that balloon 320 and delivery cannula 330 are upstream of the narrowed lumen of LCX 170 (block 410). Angiographic or fluoroscopic techniques may be used to place catheter assembly 300. Once balloon 320 is placed and subject to low inflation pressure, guidewire 318 is removed and replaced in one embodiment with an optical fiber. In the catheter assembly shown in FIG. 9, the imaging portion of an imaging device (e.g., OCT, ultrasonic, etc.) may be within the imaging lumen as the catheter is positioned. Once positioned, in this case upstream of occlusion 185, the imaging assembly is utilized to view the blood vessel and identify the various layers of the blood vessel (block 420).

The imaging assembly provides viewable information about the thickness or boundary of the intimal layer 110, media layer 120, and adventitial layer 130 of LCX 170 (See FIG. 1). The imaging assembly may also be used to measure a thickness of a portion of the blood vessel wall at the location, e.g., the thickness of the various layers of LCX 170.

LCX 170 is viewed and the layer boundary is identified or a thickness of a portion of the blood vessel wall is imaged (and possibly measured) (block 420). The treatment site may be identified based on the imaging (and possible measuring) (block 430). In one example, the treatment site is a peri-adventitial site (e.g., site 190) adjacent to LCX 170. At this point, balloon 320 is dilated as shown in FIG. 4 by, for example, delivering a fluid to balloon 320 through inflation cannula 328. The inflation of balloon 320 causes delivery cannula 330 to move proximate to or contact the blood vessel wall adjacent to the treatment site. Needle 334 is then advanced a distance into the wall of the blood vessel (block 440). A real time image may be used to advance needle 334. Alternatively, the advancement may be based on a measurement of the blood vessel wall or layer boundary derived from an optical image.

In the embodiment shown in FIG. 10, needle 334 is advanced through the wall of LCX 170 to peri-adventitial site 190. Needle 334 is placed at a safe distance, determined by the measurement of a thickness of the blood vessel wall and the proximity of the exit of delivery cannula 330 to the blood vessel wall. Once in position, a treatment agent, such as a treatment agent including a cellular component, is introduced through needle 334 to the treatment site (e.g., peri-adventitial site 190) (block 450).

Figure 12:
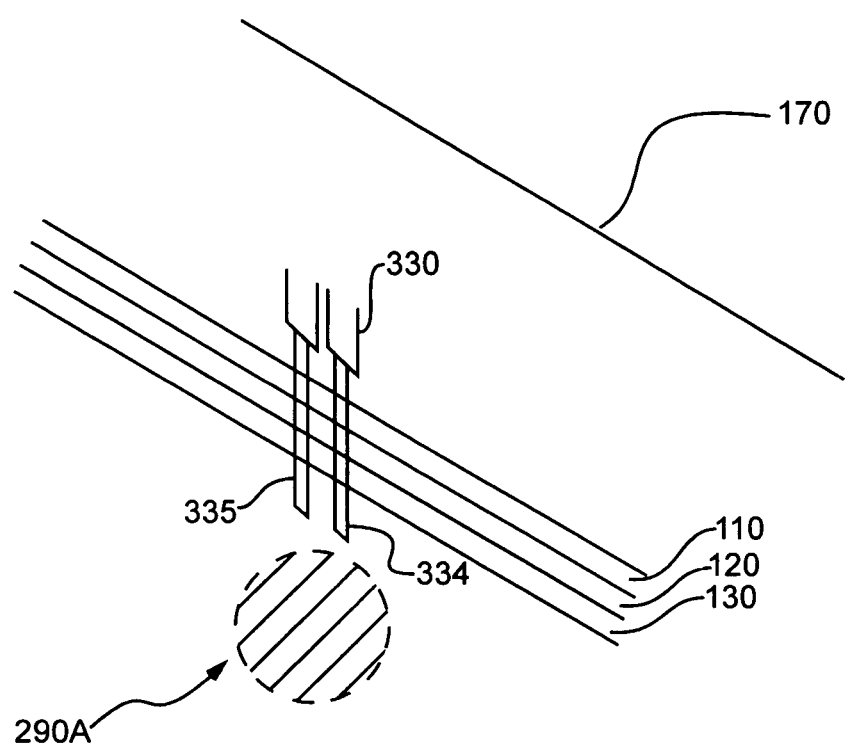
FIG. 12 schematically illustrate the portion of the coronary artery network of FIG. 2 having a catheter assembly introduced therein according to another embodiment.

FIG. 12 shows an embodiment where two needles are inserted through a blood vessel. The two needles are adjacent one another. Representatively, the catheter assembly described with reference to FIG. 4 may be utilized to introduce two adjacent needles. Reference to that catheter assembly is used in FIG. 12.

FIG. 12 shows needle 334 (and delivery cannula 330) and needle 335 advanced through the wall of LCX 170 to myocardial tissue site 290A (see FIG. 3). The technique described above with reference to FIG. 10 and FIG. 11 may be employed to locate needle 334 and needle 335 at myocardial tissue site 290A. Once in position, a treatment agent, such as a treatment agent including a cellular component may be introduced through needle 334 to the treatment site (e.g., myocardial tissue site 290A). In one embodiment, a suitable treatment agent is combined with a matrix or gel precursor, such as a modified alginate. Accordingly, to form a matrix or gel, a suitable second precursor is introduced through needle 335. With needle 334 and needle 335 adjacent one another, the two precursors may interact, combine and/or react to form a matrix or gel of myocardial tissue site 290A.

In the above described embodiment of locating a treatment agent within or beyond a blood vessel wall (e.g., at a peri-adventitial site), it is appreciated that an opening is made in or through the blood vessel. In same instances, it may be desirable to plug or fill the opening following delivery of the treatment agent. This may be accomplished by introduction of cyanoacrylate or similar material that will harden on contact with blood.

In the above embodiments, an illustration and method was described to introduce a treatment agent at a peri-adventitial site and to a myocardial tissue site. It is appreciated that the treatment agent may be introduced to a portion of the wall of the blood vessel. In another embodiment, the introduction is at a point beyond the media layer (e.g., beyond media layer 120 in FIG. 1) to the adventitial layer (e.g., adventitial layer 130 in FIG. 1). Further, in the above embodiments, reference to introduction of a treatment agent including a cellular component is made to induce and/or modulate therapeutic angiogenesis and/or therapeutic angiomyogenesis. It is appreciated that additional therapeutic treatment agents (e.g., drugs, growth factors, inflammation inducing agents, etc.) may additionally be introduced along with or separate from a treatment agent including a cellular component where desired.

Still further, in the catheter assembly described with reference to FIG. 4 and the embodiment with reference to FIG. 9, single balloon catheter assemblies are illustrated. It is appreciated that a suitable catheter assembly may include multiple balloons (e.g., in series or tandem). Representative multiple balloon assemblies are described in commonly-owned, U.S. patent application Ser. No. 10/394,834 (filed Mar. 20, 2003), titled "Drug Delivery Catheter with Retractable Needle," of Chow et al.; and U.S. patent application Ser. No. 10/749,354 (filed Dec. 31, 2003), titled "Needle Catheter." of Chan, et al. Each balloon in a multiple balloon catheter assembly may function in a similar way (e.g., to deliver a treatment agent to a wall of a blood vessel or beyond a wall of a blood vessel) or differently (e.g., one balloon to deliver a stent a second balloon to deliver a treatment agent) In the case of co-injection of precursors that interact, combine, or react with one another, a first precursor including a treatment may be introduced off of one balloon, while a second precursor may be introduced off a second adjacent balloon.

In the preceding detailed description, the invention is described with reference to specific embodiments is made. It will, however, be evident that various modifications and changes may be made thereto without departing from the broader spirit and scope of claims. The specification and drawings are, accordingly, to be regarded in an illustrative rather than a restrictive sense.

What is claimed is:

1. A method comprising:
   positioning a delivery device at a location in a blood vessel, the delivery device comprising a balloon;
   positioning an imaging device disposed within a lumen of the delivery device at the location, the lumen dimensioned to be shared simultaneously or sequentially with a guidewire and comprising a plug member to divide the lumen into a first region and a second region distal to the first region, the imaging device is positioned within the first region and the second region is operable to accommodate a guidewire;
   imaging with the positioned imaging device and measuring a thickness of a portion of a wall of the blood vessel at the location;
   identifying a treatment site beyond an external elastic lamina of the blood vessel based on the imaging and measuring;

after identifying the treatment site, inflating the balloon;

after inflating the balloon, advancing a needle from a delivery cannula coupled to an exterior surface of the balloon a distance into the wall of the blood vessel to the identified treatment site beyond an external elastic lamina of the blood vessel; and after advancing the needle, introducing a treatment agent comprising a cellular component from the needle.

2. The method of claim 1, wherein imaging of a portion of a wall of the blood vessel comprises ultrasonic imaging the portion of the blood vessel wall.

3. The method of claim 1, wherein imaging of a portion of a wall of the blood vessel comprises optical imaging the portion of the vessel wall.

4. The method of claim 1, wherein the treatment site comprises a peri-adventitial space.

5. The method of claim 1, wherein the treatment site comprises a site radially outward from a peri-adventitial space.

6. The method of claim 1, wherein positioning comprises positioning a delivery port for the needle at a position upstream from an obstruction in the blood vessel.

7. The method of claim 1, wherein the blood vessel is part of a network and another blood vessel in the network other than the blood vessel wherein the catheter is positioned comprises an obstruction.

8. The method of claim 1, wherein introducing the treatment agent further comprises introducing at least one of a cell adhesion ligand, a homing molecule, and a preservation molecule.

9. The method of claim 8, wherein the cell adhesion ligand comprises a portion of a matrix material.

10. The method of claim 9, wherein the matrix material comprises a non-immunogenic collagen.

11. The method of claim 9, wherein the matrix material comprises a hydrogel.

12. The method of claim 11, wherein the hydrogel comprises a modified alginate.

13. The method of claim 11, wherein the matrix material comprises at least one of a homing molecule and a preservation molecule therein, the at least one of a homing molecule and a preservation molecule being separate from the cellular component.

14. The method of claim 13, wherein the at least one of a homing molecule and a preservation molecule is embodied in one of a protein and a peptide.

15. The method of claim 1, wherein the treatment agent comprising a cellular component has a property to induce at least one of angiogenesis, arteriogenesis and angiomyogenesis.

16. The method of claim 1, wherein introducing the treatment agent comprises:

introducing separately a portion of a matrix material and a treatment agent comprising a cellular component.

17. The method of claim 16, further comprising forming a gelatinous matrix of the portion of the matrix material and the treatment agent in situ.

18. The method of claim 17, wherein the portion of the matrix material is a first portion material and the treatment agent is introduced with a second portion of a matrix material comprising a modified alginate, wherein the first portion of the matrix material comprises a salt suitable to react with the alginate.

19. The method of claim 17, wherein the portion of the matrix material is a first portion comprising a first ionic polymer and the treatment agent is introduced with a second portion of a matrix material suitable to react with the first ionic polymer.

20. The method of claim 16, wherein the needle comprises a first needle and the delivery cannula comprises a first cannula, and introducing separately comprises introducing the portion of the matrix material through the first needle and the treatment agent through a second needle from a second delivery cannula disposed outside of the lumen of the delivery device.

* * * * *